United States Patent
Yun et al.

(10) Patent No.: US 10,835,134 B2
(45) Date of Patent: Nov. 17, 2020

(54) METHODS AND COMPOSITIONS FOR RESTORING HOMEOSTATIC CAPACITY OF A SUBJECT

(71) Applicant: Palo Alto Investors, Palo Alto, CA (US)

(72) Inventors: Anthony Joonkyoo Yun, Menlo Park, CA (US); Conrad Minkyoo Yun, San Mateo, CA (US)

(73) Assignee: Palo Alto Investors, Palo Alto, CA (US)

( * ) Notice: Subject to any disclaimer, the term of this patent is extended or adjusted under 35 U.S.C. 154(b) by 416 days.

(21) Appl. No.: 14/737,248

(22) Filed: Jun. 11, 2015

(65) Prior Publication Data

US 2015/0359888 A1 Dec. 17, 2015

Related U.S. Application Data

(60) Provisional application No. 62/012,093, filed on Jun. 13, 2014, provisional application No. 62/012,083, filed on Jun. 13, 2014, provisional application No. 62/128,816, filed on Mar. 5, 2015.

(51) Int. Cl.

| | | |
|---|---|---|
| *A61B 5/024* | (2006.01) | |
| *A61N 1/05* | (2006.01) | |
| *A61N 1/36* | (2006.01) | |
| *A61K 31/00* | (2006.01) | |
| *A61K 45/06* | (2006.01) | |
| *A61B 5/00* | (2006.01) | |
| *A61B 5/16* | (2006.01) | |
| *G16H 50/30* | (2018.01) | |
| *G16H 20/00* | (2018.01) | |
| *A61B 5/021* | (2006.01) | |
| *A61B 5/0408* | (2006.01) | |
| *A61B 5/0456* | (2006.01) | |

(52) U.S. Cl.
CPC .......... *A61B 5/02405* (2013.01); *A61B 5/165* (2013.01); *A61B 5/4035* (2013.01); *A61B 5/4848* (2013.01); *A61B 5/7275* (2013.01); *A61K 31/00* (2013.01); *A61K 45/06* (2013.01); *A61N 1/0551* (2013.01); *A61N 1/36053* (2013.01); *A61N 1/36139* (2013.01); *G16H 20/00* (2018.01); *G16H 50/30* (2018.01); *A61B 5/021* (2013.01); *A61B 5/024* (2013.01); *A61B 5/0408* (2013.01); *A61B 5/0456* (2013.01); *A61B 5/486* (2013.01); *A61B 5/4806* (2013.01); *A61B 2505/09* (2013.01); *A61N 1/3606* (2013.01); *A61N 1/36031* (2017.08)

(58) Field of Classification Search
CPC ... A61B 5/02405; A61B 5/165; A61B 5/4035; A61B 5/4848; A61B 5/7275; A61B 5/42; A61B 5/4227; A61K 31/00; A61K 45/06; A61N 1/36014; A61N 1/36053; A61N 1/3606; A61N 1/36139; A61N 1/3627; A61N 1/3629; A61N 1/36514; A61N 1/3962; A61M 5/1723; A61P 5/00; A61P 5/02; A61P 5/04; A61P 5/06; A61P 5/08; A61P 5/10; A61P 5/12; A61P 5/14; A61P 5/16; A61P 5/18; A61P 5/20; A61P 5/22; A61P 5/38; A61P 5/40; A61P 5/42; A61P 5/44; A61P 5/46; A61P 5/48; A61P 5/50
USPC ........................................................ 600/301
See application file for complete search history.

(56) References Cited

U.S. PATENT DOCUMENTS

| | | | |
|---|---|---|---|
| 7,020,521 B1 * | 3/2006 | Brewer | A61N 1/3627 607/14 |
| 7,149,574 B2 | 12/2006 | Yun et al. | |
| 7,363,076 B2 | 4/2008 | Yun et al. | |
| 7,676,269 B2 | 3/2010 | Yun et al. | |
| 7,738,952 B2 | 6/2010 | Yun et al. | |
| 7,767,713 B2 | 8/2010 | Yun et al. | |
| 7,899,527 B2 | 3/2011 | Yun et al. | |
| 7,966,072 B2 | 6/2011 | Yun et al. | |
| 8,121,690 B2 | 2/2012 | Yun et al. | |
| 8,247,450 B2 | 8/2012 | Yun et al. | |
| 8,457,745 B1 * | 6/2013 | Garcia | A61N 1/36053 607/40 |
| 8,491,459 B2 | 7/2013 | Yun | |
| 8,569,277 B2 | 10/2013 | Yun et al. | |
| 8,571,650 B2 | 10/2013 | Yun | |

(Continued)

FOREIGN PATENT DOCUMENTS

| | | |
|---|---|---|
| JP | 2000-262480 A | 9/2000 |
| KR | 10-131528 B1 | 10/2013 |

OTHER PUBLICATIONS

Russoniello et al., Heart rate variability and biological age: implications for health and gaming, Cyberpsychol Behav Soc Netw. Apr. 2013;16(4):302-8.

*Primary Examiner* — Kevin C Sirmons
*Assistant Examiner* — Alexandra Lalonde
(74) *Attorney, Agent, or Firm* — Peter W. Schroen; Bret E. Field; Bozicevic, Field & Francis LLP

(57) ABSTRACT

Methods of restoring homeostatic capacity of a subject are provided. Aspects of the invention further include compositions, systems and devices for practicing the methods. The methods and compositions described herein find use in a variety of applications. Aspects of certain embodiments of the methods include modulating a subject's autonomic nervous system in a manner sufficient to restore the homeostatic capacity of the subject. Aspects of other embodiments of the invention include administering to the subject an amount of an apoptosis modulator effective to at least partially restore homeostatic function of the neuroendocrine system of the subject.

20 Claims, No Drawings

(56) References Cited

U.S. PATENT DOCUMENTS

| | | | |
|---|---|---|---|
| 8,691,877 B2 | 4/2014 | Yun et al. | |
| 8,722,016 B2 | 5/2014 | Yun | |
| 8,788,041 B2 | 7/2014 | Yun et al. | |
| 8,909,340 B2 | 12/2014 | Yun | |
| 2003/0097151 A1 | 5/2003 | Smedley et al. | |
| 2003/0195427 A1* | 10/2003 | Masakov | A61B 5/0205 600/483 |
| 2004/0086576 A1 | 5/2004 | Cianfarani | |
| 2004/0230252 A1* | 11/2004 | Kullok | A61M 21/00 607/48 |
| 2004/0249416 A1 | 12/2004 | Yun et al. | |
| 2005/0015122 A1 | 1/2005 | Mott et al. | |
| 2005/0021092 A1 | 1/2005 | Yun et al. | |
| 2005/0143788 A1 | 6/2005 | Yun et al. | |
| 2005/0153885 A1 | 7/2005 | Yun et al. | |
| 2005/0192637 A1* | 9/2005 | Girouard | A61M 5/1723 607/3 |
| 2005/0240241 A1 | 10/2005 | Yun et al. | |
| 2005/0256028 A1 | 11/2005 | Yun et al. | |
| 2005/0288721 A1 | 12/2005 | Girouard et al. | |
| 2006/0034847 A1 | 2/2006 | Yun et al. | |
| 2006/0035974 A1 | 2/2006 | Yun et al. | |
| 2006/0069012 A1 | 3/2006 | Yun et al. | |
| 2006/0116721 A1 | 6/2006 | Yun et al. | |
| 2006/0190052 A1 | 8/2006 | Yun et al. | |
| 2006/0206149 A1 | 9/2006 | Yun | |
| 2006/0216251 A1 | 9/2006 | Morariu | |
| 2007/0054871 A1 | 3/2007 | Pastore et al. | |
| 2007/0112327 A1 | 5/2007 | Yun et al. | |
| 2007/0208382 A1 | 9/2007 | Yun | |
| 2008/0075665 A1 | 3/2008 | Yun | |
| 2009/0202659 A1 | 8/2009 | Gimble | |
| 2010/0119482 A1 | 5/2010 | Yun et al. | |
| 2010/0144691 A1 | 6/2010 | Yun et al. | |
| 2010/0217358 A1 | 8/2010 | Hebert et al. | |
| 2010/0260669 A1 | 10/2010 | Yun et al. | |
| 2010/0262220 A1 | 10/2010 | Yun | |
| 2010/0280116 A1 | 11/2010 | Yun et al. | |
| 2010/0286734 A1 | 11/2010 | Yun et al. | |
| 2010/0332443 A1 | 12/2010 | Gartenberg | |
| 2011/0015188 A1 | 1/2011 | Yun et al. | |
| 2011/0029030 A1 | 2/2011 | Yun et al. | |
| 2011/0152967 A1* | 6/2011 | Simon | A61N 1/40 607/45 |
| 2011/0256097 A1 | 10/2011 | Yun et al. | |
| 2012/0102937 A1 | 5/2012 | Anikhindi et al. | |
| 2012/0270876 A1 | 10/2012 | Yun et al. | |
| 2013/0053817 A1 | 2/2013 | Yun | |
| 2013/0158423 A1 | 6/2013 | Kapoor | |
| 2014/0024079 A1 | 1/2014 | Yun | |
| 2014/0052211 A1 | 2/2014 | Yun | |
| 2014/0065129 A1 | 3/2014 | Yun et al. | |
| 2014/0086872 A1 | 3/2014 | Yun et al. | |
| 2014/0248217 A1 | 9/2014 | Yun | |
| 2014/0303236 A1 | 10/2014 | van Rooij et al. | |
| 2014/0350041 A1 | 11/2014 | Yun et al. | |
| 2014/0369969 A1 | 12/2014 | Yun | |
| 2015/0025924 A1 | 1/2015 | Yun et al. | |
| 2015/0087608 A1 | 3/2015 | Yun | |
| 2015/0283265 A1 | 10/2015 | Peyman | |
| 2016/0213296 A1 | 7/2016 | Kikuchi et al. | |
| 2016/0375240 A1 | 12/2016 | Yanaki et al. | |
| 2018/0362623 A1 | 12/2018 | Tseng et al. | |

* cited by examiner

METHODS AND COMPOSITIONS FOR RESTORING HOMEOSTATIC CAPACITY OF A SUBJECT

CROSS-REFERENCE TO RELATED APPLICATIONS

This application claims the benefit of U.S. Provisional Application Nos. 62/012,093, filed Jun. 13, 2014; 62/012,083, filed Jun. 13, 2014; and 62/128,816, filed Mar. 5, 2015, which applications are incorporated herein by reference in their entireties and for all purposes.

INTRODUCTION

Homeostasis refers to the tendency of biological systems to maintain relatively constant conditions in the internal environment while continuously interacting with and adjusting to changes originating within or outside the system. Homeostasis actually involves continuous motion, adaptation, and change in response to environmental factors. It is through homeostatic mechanisms that body temperature is kept within normal range, the osmotic pressure of the blood and its hydrogen ion concentration (pH) is kept within strict limits, nutrients are supplied to cells as needed, and waste products are removed before they accumulate and reach toxic levels of concentration. These are but a few examples of the thousands of homeostatic control systems within the body. Some of these systems operate within the cell and others operate within an aggregate of cells (organs) to control the complex interrelationships among the various organs.

Homeostatic capacity refers to the capability of systems, such as described above, to self-stabilize in response to stressors. A simple way to visualize homeostatic capacity is to imagine a Weeble™, the popular self-centering children's toy. For organisms, it is life's foundational trait—itself comprised of a hierarchy and network of traits—endowed by nature and shaped by selection. Because the trait is inborn and so pervasively effective, feeling healthy feels like "nothing" when we are young. We become aware of it only after we start losing it midlife. Roller-coaster rides begin to leave us nauseated instead of joyous. We can't tolerate hot or cold weather like before. Sunny days feel too bright and reading menus in low lights becomes more difficult. Recovering from stressors—a late night, hangover, or injury—suddenly take far longer than it used to, if at all. Consider changes that we can't feel. When we are young, homeostatic capacity returns elevated blood glucose and blood pressure to base levels. As homeostatic capacity erodes with age, those levels may no longer self-tune.

There are a variety of conditions that can affect an individual's health and well-being. The treatment of various conditions that affect the health and well-being of an individual has been around for centuries. Such treatments include pharmacological, surgical, and life style (dietetic, exercise, etc.) changes. In general, the armament of treatment options available to a physician to treat such conditions has increased tremendously, especially in the last century.

However, while the number of treatment options has increased, typically such options are merely palliative, i.e., are designed for the relief of symptoms of a condition rather than actually being curative of the disorder itself. In fact, treatment protocols effectively directed at the underlying cause of a condition are quite rare.

As such, there continues to be an interest in the development of new protocol options for treating conditions. Of particular interest are protocols for treating conditions that are directed at the cause of the condition rather than the symptoms thereof.

SUMMARY

Methods of restoring homeostatic capacity of a subject are provided. Aspects of certain embodiments of the methods include modulating a subject's autonomic nervous system in a manner sufficient to restore the homeostatic capacity of the subject. Aspects of other embodiments of the invention include administering to the subject an amount of an apoptosis modulator effective to at least partially restore homeostatic function of the neuroendocrine system of the subject. Aspects of the invention further include compositions, systems and devices for practicing the methods. The methods and compositions described herein find use in a variety of applications.

DETAILED DESCRIPTION

Methods of restoring homeostatic capacity of a subject are provided. Aspects of embodiments of the methods include modulating a subject's autonomic nervous system in a manner sufficient to restore the homeostatic capacity of the subject. Aspects of other embodiments of the invention include administering to the subject an amount of an apoptosis modulator effective to at least partially restore homeostatic function of the neuroendocrine system of the subject. Aspects of the invention further include compositions, systems and devices for practicing the methods. The methods and compositions described herein find use in a variety of applications.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Methods recited herein may be carried out in any order of the recited events which is logically possible, as well as the recited order of events.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It must be noted that as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

In further describing the invention, aspects of embodiments of methods of the invention are described first in greater detail, followed by a description of representative devices that find use in practicing various embodiments of the methods.

Methods

As summarized above, the subject methods provided herein are methods for at least partially restoring homeostatic capacity of a subject. Homeostatic capacity refers to the ability of a subject to maintain relatively constant conditions in the internal environment while continuously interacting with and adjusting to changes originating within or outside the system. By at least partially restoring the homeostatic capacity of the subject is meant that the homeostatic capacity of the subject is restored to be normal. By "normal" is meant the homeostatic capacity of a healthy subject of a particular age. In certain embodiments, the healthy subject is a healthy human 18 year old, 19 year old, 20 year old, 21 year old, 22 year old, 23 year old, 24 year old, 25 year old, 26 year old, 27 year old, 28 year old, 29 year old, 30 year old, 31 year old, 32 year old, 33 year old 34 year old, 35 year old, 36 year old, 37 year old, 38 year old, 39 year old, 40 year old, 41 year old, 42 year old, 43 year old, 44 year old, 45 year old, 46 year old, 47 year old, 48 year old, 49 year old or 50 year old. In some instances, the normal function with respect to homeostatic capacity is that of a healthy human 25 year old.

Restoration of the homeostatic capacity of a subject so that it is at least closer to that of a healthy human (e.g., a healthy human 25 year old) can be achieved using any suitable protocol, including, but not limited to electrical and/or pharmacologic protocols and/or homeostatic function restoration, as described below. By "at least closer" is meant, in some instances, that the target homeostatic capacity is restored to be 50% or more, e.g., 75% or more of the target function, such as 80% or more of the target function, including 90% or more of the target function, e.g., 95% or more of the target function, including 99% or more of the target function. Homeostatic capacity of a subject can be assayed using any suitable method, e.g., as described in greater detail below.

Embodiments of the methods result in rapid restoration of homeostatic capacity of the subject. For example, in some instances homeostatic capacity may be restored in 72 hours or less relative to the onset of autonomic modulation, such as in 48 hours or less, 24 hours or less, or 12 hours or less relative to the onset of autonomic modulation.

ANS Modulation

As summarized above, in certain embodiments, homeostatic capacity is at least partially restored in a subject by modulating the autonomic nervous system of the subject. The autonomic nervous system ("ANS") is that portion of the nervous system that is not the somatic nervous system. The ANS controls individual organ function and homeostasis. For the most part, the ANS is not subject to voluntary control. The ANS is also commonly referred to as the visceral or automatic system. The ANS can be viewed as a "real-time" regulator of physiological functions that extracts features from the environment and, based on that information, allocates an organism's internal resources to perform physiological functions for the benefit of the organism, e.g., responds to environment conditions in a manner that is advantageous to the organism. The ANS conveys sensory impulses to and from the central nervous system to various structures of the body such as organs and blood vessels, in addition to conveying sensory impulses through reflex arcs. For example, the ANS controls constriction and dilatation of blood vessels; heart rate; the force of contraction of the heart; contraction and relaxation of smooth muscle in various organs; lungs; stomach; colon; bladder; visual accommodation, secretions from exocrine and endocrine glands, etc. The ANS does this through a series of nerve fibers and more specifically through efferent and afferent nerves.

The ANS acts through a balance of its two components: the sympathetic nervous system and parasympathetic nervous system, which are two anatomically and functionally distinct systems. Both of these systems include myelinated preganglionic fibers which make synaptic connections with unmyelinated postganglionic fibers, and it is these fibers which then innervate the effector structure. These synapses usually occur in clusters called ganglia. Most organs are innervated by fibers from both divisions of the ANS, and the influence is usually opposing (e.g., the vagus nerve slows the heart, while the sympathetic nerves increase its rate and contractility), although it may be parallel (e.g., as in the case of the salivary glands).

By "modulating" is meant altering or changing one aspect or component to provide a change, alteration or shift in another aspect or component. Modulating autonomic function is achieved by modulating at least one portion of the subject's autonomic nervous system. By "modulating at least one portion of the subject's autonomic nervous system" is meant altering or changing at least a portion of an autonomic nervous system by a means to provide a change, alteration or shift in at least one component or aspect of the autonomic nervous system.

In some instances of the subject methods, modulation of the autonomic nervous system includes modulating the parasympathetic and/or sympathetic activity in the subject. "Parasympathetic activity" refers to activity of the parasympathetic nervous system whereas "sympathetic activity" refers to activity of the sympathetic nervous system.

In some instances, modulation results in at least one of decreasing parasympathetic activity and/or increasing sympathetic activity in a subject to improve a condition caused by parasympathetic bias. In other embodiments, the modulation results in at least one of decreasing sympathetic activity and/or increasing parasympathetic activity in a subject to improve a condition caused by sympathetic bias.

Modulation of the autonomic nervous system may be carried out using any suitable protocol, including, but not limited to electrical and/or pharmacologic protocols as described below. The pharmacological and/or electrical modulation of the ANS may provide an increase in function of at least a portion of the autonomic system, e.g., increase function in at least one sympathetic or parasympathetic nerve fiber, and/or provide a decrease in function or dampening of a portion of the autonomic system, e.g., may inhibit activity in at least one sympathetic or parasympathetic nerve fiber or inhibit nerve pulse transmission.

In some instances, the modulation that is achieved in practicing methods of the invention may be quantified. One way of quantifying modulation of at least one portion of the subject's autonomic nervous system is the parasympathetic/sympathetic activity ratio. By "parasympathetic/sympathetic activity ratio" is meant the ratio of activity of the sympathetic nervous system to the activity of the parasympathetic nervous system. As such, methods according to certain embodiments include modulating a sympathetic/parasympathetic activity ratio in the subject.

In some instances, the ANS is modulated in such a manner to shift or change parasympathetic activity and/or sympathetic activity from a first state to a second state, where the second state is characterized by an increase or decrease in the sympathetic activity/parasympathetic activity ratio relative to the first state.

Accordingly, some embodiments of the subject invention include modulating at least a portion of a subject's autonomic nervous system to increase the sympathetic activity/parasympathetic activity ratio, i.e., to increase sympathetic activity relative to parasympathetic activity (in other words to decrease parasympathetic activity relative to sympathetic activity) so as to treat a subject for a condition that can be treated by such modulation (e.g., a condition caused by parasympathetic bias). Alternatively or in addition to stimulating at least one sympathetic nerve fiber to increase activity, increasing the sympathetic activity/parasympathetic activity ratio may be achieved by inhibiting activity in the parasympathetic system.

Other embodiments of the subject invention include modulating a subject's autonomic nervous system to decrease the sympathetic activity/parasympathetic activity ratio, i.e., to decrease sympathetic activity relative to parasympathetic activity (in other words, to increase parasympathetic activity relative to sympathetic activity) so as to treat a subject for a condition that can be treated by such modulation (e.g., a condition caused by sympathetic bias).

As will be described in greater detail below, while the ratio of sympathetic function/parasympathetic function may be modulated according to embodiments of the subject invention to treat or improve a subject for a condition (e.g., aging associated conditions) the net result may be a parasympathetic bias (i.e., a parasympathetic dominance), a sympathetic bias (i.e., sympathetic dominance), or the activities of the sympathetic system and parasympathetic system may be substantially equal (i.e., neither is dominant).

By "bias", is meant that the particular "biased" component of the autonomic nervous system has a higher activity level than the other component. For example, a parasympathetic bias refers to a higher level of parasympathetic activity than sympathetic activity, and vice versa, where such bias may be systemic or localized. As such, by "vagal bias", is meant that that the particular biased component of the autonomic nervous system that has a higher activity level than the other component is the vagus nerve or a portion of the autonomic nervous system associated with the vagus nerve. Vagal bias may be characterized by one or more of vagal dominance, vagal hypersensitivity and/or sympathetic insufficiency. The net result of the subject methods to treat a condition may be higher or greater sympathetic activity relative to parasympathetic activity in at least the area of the targeted autonomic system (i.e., that portion in need of modulation), or substantially equal activity levels of sympathetic activity and parasympathetic activity.

As noted above, in certain embodiments activity in at least a portion of the autonomic nervous system is increased. For example, activity in at least a portion of the ANS that is involved the sympathetic nervous system may be increased such that at least a portion of the sympathetic nervous system may be "up-regulated". In other instances, any portion of the ANS that is involved in the parasympathetic system, e.g., one or more nerve fibers, may be stimulated to increase parasympathetic activity to provide the desired ratio of parasympathetic/sympathetic activity. In other words, activity in at least a portion of the parasympathetic nervous system may be increased such that at least a portion of the parasympathetic nervous system may be "up-regulated".

In certain embodiments, increasing activity in, or up-regulating, at least a part of the sympathetic system may be desired in instances where, prior to the application of autonomic nervous system-modulating agent, parasympathetic activity is higher than desired, e.g., higher than sympathetic activity (e.g., there exists a relative parasympathetic bias) and as such the subject methods may be employed to increase sympathetic activity to a level above or rather to a level that is greater than parasympathetic activity or may be employed to modulate the differential between the parasympathetic-sympathetic systems such that the result of increasing sympathetic activity may be a sympathetic bias, parasympathetic bias or may be an equalization of the two systems (i.e., the activities of the two systems are approximately equal—including equal), but the difference between the parasympathetic-sympathetic systems may be modulated, e.g., reduced or minimized or increased in certain embodiments. Accordingly, the subject methods may be employed to increase sympathetic activity above that of parasympathetic activity and/or may be employed to modulate (increase or decrease) the differential between the two systems, but in certain embodiments may be employed to decrease the parasympathetic activity/sympathetic activity ratio.

In other embodiments, increasing activity in, or up-regulating, at least a part of the parasympathetic system may be desired in instances where, prior to the application of autonomic nervous system-modulating agent, sympathetic activity is higher than desired, e.g., higher than parasympathetic activity (e.g., there exists a relative sympathetic bias) and as such the subject methods may be employed to increase parasympathetic activity to a level above or rather to a level that is greater than sympathetic activity or may be employed to modulate the differential between the parasympathetic-sympathetic systems such that the result of increasing parasympathetic activity may be a parasympathetic bias, sympathetic bias or may be an equalization of the two systems (i.e., the activities of the two systems are approximately equal—including equal), but the difference between the parasympathetic-sympathetic systems may be modulated, e.g., reduced or minimized or increased in certain embodiments. Accordingly, the subject methods may be employed to increase parasympathetic activity above that of sympathetic activity and/or may be employed to modulate (increase or decrease) the differential between the two systems, but in certain embodiments may be employed to decrease the parasympathetic activity/sympathetic activity ratio.

In certain embodiments, a parasympathetic bias may be the normal state, but the ratio of the two systems may be abnormal or otherwise contributing to a condition. Increasing sympathetic bias may also be desired in instances where, prior to the restoration of the normal function of a central nervous system endocrine gland, sympathetic activity is higher than the parasympathetic activity, but the differential between the two needs to be modulated such as increased further, e.g., the sympathetic activity is normal or above normal (i.e., abnormally high) and/or the parasympathetic activity is normal or below normal (i.e., abnormally low) or above normal (i.e., abnormally low).

For example, such instances may occur where a subject has normal or above normal sympathetic function, but also has elevated parasympathetic function. Other instances may include below normal sympathetic function, but normal or elevated parasympathetic function, etc. It may also be desirable to increase sympathetic function in instances where the respective activities of the two system are analogous or approximately equal, including equal, prior to increasing activity in the sympathetic system, but the level of one or both is abnormally high or abnormally low. The above-described examples of instances where increasing sympathetic activity may be desired is exemplary only and is in no way intended to limit the scope of the invention and other instances where increasing sympathetic activity may be desired will be apparent to those of skill in the art.

In other embodiments, a sympathetic bias may be the normal state, but the ratio of the two systems may be abnormal or otherwise contributing to a condition. Increasing parasympathetic bias may also be desired in instances where, prior to the restoration of the normal function of a central nervous system endocrine gland, parasympathetic activity is higher than the sympathetic activity, but the differential between the two needs to be modulated such as increased further, e.g., the parasympathetic activity is normal or above normal (i.e., abnormally high) and/or the sympathetic activity is normal or below normal (i.e., abnormally low) or above normal (i.e., abnormally low).

For example, such instances may occur where a subject has normal or above normal parasympathetic function, but also has elevated sympathetic function. Other instances may include below normal parasympathetic function, but normal or elevated sympathetic function, etc. It may also be desirable to increase parasympathetic function in instances where the respective activities of the two system are analogous or approximately equal, including equal, prior to increasing activity in the parasympathetic system, but the level of one or both is abnormally high or abnormally low. The above-described examples of instances where increasing parasympathetic activity may be desired is exemplary only and is in no way intended to limit the scope of the invention and other instances where increasing sympathetic activity may be desired will be apparent to those of skill in the art.

As noted above, in certain embodiments, activity in at least a portion of the ANS may be inhibited to modulate at least a portion of the autonomic nervous system. Inhibiting or "down-regulating" activity in at least a part of the autonomic nervous system, may be desired in instances where, the sympathetic or parasympathetic activity is higher than desired. For example, parasympathetic activity may be higher than the sympathetic activity (i.e., there exists a parasympathetic bias) or parasympathetic activity may be less than or approximately equal to, including equal, to sympathetic activity, and the subject methods may be employed to modulate the differential between the parasympathetic-sympathetic systems such that the net result of decreasing sympathetic activity may be a sympathetic bias, parasympathetic bias or may be an equalization of the two systems (i.e., the activities of the two systems are approximately equal—including equal), but the difference between the parasympathetic-sympathetic systems may be modulated, e.g., increased or reduced in certain embodiments.

Accordingly, the subject methods may be employed to decrease parasympathetic activity below that of sympathetic activity and/or may be employed to modulate (decrease or increase) the differential between the two systems, where in certain embodiments may be employed to decrease the ratio of parasympathetic activity to sympathetic activity.

For example, decreasing activity in at least a portion of the parasympathetic system may be employed where there is a normal or an abnormally low sympathetic function and/or abnormally high parasympathetic function. Such may also be desired in instances where, prior to decreasing parasympathetic function in, e.g., at least one parasympathetic nerve fiber, sympathetic activity is higher than the parasympathetic activity, but the differential between the two needs to be increased further. For example, such instances may occur where a subject has normal or above normal (i.e., abnormally high) parasympathetic function, but also has elevated sympathetic function (i.e., abnormally high), e.g., a relative bias towards sympathetic function may be present. Other instances include normal or below normal (i.e., abnormally low) parasympathetic activity and/or normal or above normal (i.e., abnormally high) sympathetic activity. The above-described examples of instances where decreasing parasympathetic activity may be desired is exemplary only and is in no way intended to limit the scope of the invention and other instances where decreasing parasympathetic activity to provide an increase in the parasympathetic activity/sympathetic activity ratio may be desired will be apparent to those of skill in the art.

Decreasing activity in at least a portion of the sympathetic system may be employed where there is a normal or an abnormally low parasympathetic function and/or abnormally high sympathetic function. Such may also be desired in instances where, prior to decreasing sympathetic function in, e.g., at least one parasympathetic nerve fiber, parasympathetic activity is higher than the sympathetic activity, but the differential between the two needs to be increased further. For example, such instances may occur where a subject has normal or above normal (i.e., abnormally high) sympathetic function, but also has elevated parasympathetic function (i.e., abnormally high), e.g., a relative bias towards parasympathetic function may be present. Other instances include normal or below normal (i.e., abnormally low) sympathetic activity and/or normal or above normal (i.e., abnormally high) parasympathetic activity. The above-described examples of instances where decreasing sympathetic activity may be desired is exemplary only and is in no way intended to limit the scope of the invention and other instances where decreasing sympathetic activity to provide an increase in the parasympathetic activity/sympathetic activity ratio may be desired will be apparent to those of skill in the art.

One way of inhibiting activity in at least a portion of the autonomic nervous system is by the application of a nerve block. Application of a nerve block at least partially prevents nerve transmission across the location of the block. A nerve block can be administered to modulate autonomic function using all the methods and devices described herein including pharmacological and/or electrical means.

As noted above, in certain embodiments, activity in at least a portion of the autonomic nervous system may be increased and activity in at least a portion of the autonomic nervous system may be decreased. For example, in certain embodiments, activity in at least a portion of the sympathetic system may be increased and activity in at least a portion of the parasympathetic system may be inhibited, e.g., to decrease the parasympathetic activity/sympathetic activity ratio. In other embodiments, activity in at least a portion of the parasympathetic system may be increased and activity in at least a portion of the sympathetic system may be inhibited, e.g., to decrease the parasympathetic activity/sympathetic activity ratio. As described above, any portion of the parasympathetic and/or sympathetic nervous systems may be modulated to increase activity and activity in any portion of the ANS may be inhibited to provide the desired ratio of parasympathetic activity to sympathetic activity. Such a protocol may be employed, e.g., in instances where sympathetic function is normal or abnormally low and/or parasympathetic function is normal or abnormally high, or where parasympathetic function is normal or abnormally low and/or sympathetic function is normal or abnormally high, where normal is determined by the typical or average autonomic nervous system functions for a healthy subject, e.g., a healthy human subject ranging in age from about 20 years old to about 25 years old.

Embodiments wherein activity in at least a portion of the autonomic nervous system may be increased and activity in at least a portion of the autonomic nervous system may be decreased may be employed to alter the dominance and/or may be employed to modulate the differential between the two systems. For example, prior to modulating the autonomic system according to the subject invention, the activity in the parasympathetic system may be higher than activity in the sympathetic system and the subject methods may be employed to increase the sympathetic activity to a level that is greater than the parasympathetic activity and/or may be employed to alter the differential or difference in activity levels of the two systems such as decreasing the difference in activity levels or increasing the difference in activity levels.

Increasing activity in at least a portion of the autonomic nervous system, e.g., increasing activity in at least a portion of the parasympathetic system, and decreasing activity in at least a portion of the autonomic nervous system, e.g., decreasing activity in at least a portion of the sympathetic system, may be performed simultaneously or sequentially such that at least a portion of the autonomic nervous system, e.g., at least a portion of the parasympathetic nervous system, may be pharmacologically and/or electrically modulated to increase activity therein prior or subsequent to inhibiting activity in at least a portion of the autonomic nervous system e.g., at least a portion of the sympathetic nervous system, such as by electrical and/or pharmacological means.

Regardless of whether increasing activity in at least a portion of the autonomic nervous system, e.g., in at least a portion of the parasympathetic system, and decreasing activity in at least a portion of the autonomic nervous system, e.g., in at least a portion of the sympathetic system, is performed simultaneously or sequentially, the parameters for increasing activity in at least a portion of autonomic nervous system and decreasing activity in at least a portion of the autonomic nervous system may be analogous to that described above.

Modulation of the autonomic nervous system may be accomplished using any suitable method, including employing electrical, thermal, vibrational, magnetic, acoustic, baropressure, optical, or other sources of energy to modulate autonomic balance, where in representative embodiments modulation is achieved via pharmacological modulation and/or electrical energy modulation in a manner that is effective to treat a subject for a food allergy syndrome condition.

Certain embodiments include pharmacologically or electrically stimulating a portion of the subject's nervous system in a manner that causes a modulation of at least a portion of a subject's autonomic nervous system, e.g., by increasing parasympathetic activity and/or decreasing sympathetic activity or by increasing sympathetic activity and/or decreasing parasympathetic activity in at least a portion of the subject's autonomic nervous system. In certain embodiments, modulation may include increasing the sympathetic activity/parasympathetic activity ratio in at least a portion of the subject's autonomic nervous system. In certain embodiments, a combination of electrical and pharmacological may be employed.

Pharmacologic Modulation

As noted above, in certain embodiments of the subject methods the ANS is pharmacologically modulated. By "pharmacologically modulation" is meant altering or changing the ANS by pharmacological means to provide a desired change, alteration or shift in autonomic function. In embodiments in which pharmacological agent is administered, any suitable protocol may be used, where certain protocols include using an pharmacological agent administering device to deliver a suitable amount of pharmacological agent to a subject. Methods and corresponding devices and systems for applying at least one pharmacological agent to a subject and which may be adapted for use in the subject invention are described, e.g., in U.S. Pat. Nos. 7,363,076; 7,149,574, U.S. patent application Ser. Nos. 10/661,368; 10/748,976; 10/871,366; 10/846,486; 10/917,270; 10/962,190; 11/060,643 11/251,629; 11/238,108; 11/592,027; 60/654,139; and 60/702,776; the disclosures of which are herein incorporated by reference.

Any convenient pharmacological agent may be employed. Pro-sympathetic agents of interest include, but are not limited to: beta agonists, e.g., dobutamine, metaproterenol, terbutaline, ritodrine, albuterol; alpha agonists, e.g., selective alpha 1-adrenergic blocking agents such as phenylephrine, metaraminol, methoxamine; prednisone and steroids, (e.g., available under the brand names CORATN, DELTASONE, LIQUID PRED, MEDICORTEN, ORASONE, PANASOL-S, PREDNICEN-M, PREDNISONE INTENSOL); indirect agents that include norepinephrine, e.g., ephedrine, ampthetamines, phenylpropanolamines, cyclopentamines, tuaminoheptanes, naphazolines, tetrahydrozolines; epinephrine; norepinephrine; acetylcholine; sodium; calcium; angiotensin I; angiotensin II; angiotensin converting enzyme I ("ACE I"); angiotensin converting enzyme II ("ACE II"); aldosterone; potassium channel blockers and magnesium channel blockers, e.g., valproate (sodium valproate, valproic acid), lithium; cocaine; amphetamines; terbutaline; dopamine; doputamine; antidiuretic hormone ("ADH") (also known as vasopressin); oxytocin (including PITOCINE); THC cannabinoids; and combinations thereof.

Pro-parasympathetic agents of interest include, but are not limited to: Beta Blockers, Aldosterone Antagonists; Angiotensin II Receptor Blockers; Angiotensin Converting Enzyme Inhibitors; Statins; Triglyceride Lowering Agents; Insulin Sensitizers; Insulin Secretagogues; Insulin Analogs; Alpha-glucosidase Inhibitors; SGLT2 Inhibitors; Immunomodulators, including agents that bind/react to CD4, gp39, B7, CD19, CD20, CD22, CD401, CD40, CD40L and CD23 antigens; Sympathomimetics; Cholinergics; Calcium Channel Blockers; Sodium Channel Blockers; Glucocorticoid Receptor Blockers; Peripheral Adrenergic Inhibitors; Blood Vessel Dilators; Central Adrenergic Agonists; Alpha-adrenergic Blockers; Combination Diuretics; Potassium-sparing Diuretics; Nitrate Pathway Modulators; Cyclic Nucleotide Monophosphodiesterase (PDE) Inhibitors; Vasopressin Inhibitors; Renin Inhibitors; Estrogen and Estrogen Analogues and Metabolites; Vesicular Monoamine Transport (VMAT) Inhibitors; Progesterone Inhibitors; Testosterone Inhibitors; Gonadotropin-releasing Hormone Inhibitors; Dipeptidyl Peptidase IV inhibitors; Anticoagulants; Thrombolytics.

Electrical Modulation

In certain embodiments, to accomplish the modulation of at least a portion of a subject's central nervous endocrine gland function (e.g., autonomic function or endocrine function), electrical energy (electrical modulation) may be applied to at least a portion of a subject's central nervous system endocrine gland, where such electrical energy may be excitatory or inhibitory and in certain embodiments may include both excitatory and inhibitory stimulation. By "electrically modulating at least a portion of a subject's autonomic nervous system" is meant altering or changing at least a portion of an autonomic nervous system by electrical means to provide a change, alteration or shift in at least one component or aspect of the function of the central nervous system endocrine gland (e.g., autonomic function or endocrine function). Embodiments of the subject methods may also, in addition to electrical energy, include administering at least one pharmacological agent (pharmacological modulation) to said subject to modulate at least a portion of a subject's central nervous system endocrine gland.

Any suitable area may be targeted for electrical modulation. Areas that may be targeted include, but are not limited to, pre- and post-ganglionic nerve fibers, as well as ganglionic structures, efferent and afferent nerve fibers, synapses, etc., and combinations thereof in certain embodiments. In certain embodiments, activity in a given nerve fiber may be electrically modulated in more than one area of the nerve fiber. In certain embodiments, electrical energy is applied to modulate synaptic efficiency. In certain embodiments, electrical energy is applied using any of the devices described below.

A number of different methods and corresponding devices and systems for applying electrical energy to a subject and which may be adapted for use in the subject invention are described, e.g., in U.S. Pat. Nos. 7,149,574; 7,711,430; and 7,363,076; as well as U.S. patent application Ser. No. 11/592,027; the disclosures of which are herein incorporated by reference.

In some instances where an electrical protocol is employed, the target condition is not a bronchoconstriction condition, such as asthma, e.g., as described in United States Patent Application 20120004701.

Paradoxical Modulation

In some instances, the methods include employing a paradoxical protocol in order to obtain a desired increase or decrease in sympathetic/parasympathetic activity ratio. In some of these embodiments, the sympathetic/parasympathetic activity ratio is increased initially in a manner effective to cause the subject to mount a compensatory response effective to ultimately decrease the sympathetic/parasympathetic activity ratio. In other embodiments, the sympathetic/parasympathetic activity ratio is decreased initially in a manner effective to cause the subject to mount a compensatory response effective to ultimately increase the sympathetic/parasympathetic activity ratio. In certain embodiments, the magnitude of increase or decrease in the sympathetic/parasympathetic activity ratio is two-fold or greater, e.g., 5-fold or greater.

In practicing the subject methods, the sympathetic/parasympathetic activity ratio is decreased by applying an appropriate stimulus to the subject, where the stimulus is of a nature and magnitude sufficient to achieve the desired enhancement. In certain embodiments, the applied stimulus is one of short duration, where by short duration is meant that the applied stimulus lasts for less than about 1 week, e.g., less than about 3 days, e.g., less than about 1 day, e.g., less than about 12 hours, where the duration of the applied stimulus may be even shorter. Where the stimulus is a pharmacological stimulus, the duration refers to the period in which the pharmacological agent from an administered dosage is active. Where the stimulus is an electrical stimulus, the duration refers to the total of electrical applications received by a subject over a given period, analogous to a dose of a pharmacological agent.

Following decrease of the sympathetic/parasympathetic activity ratio via an applied stimulus, as described above, the stimulus is removed, e.g., by metabolization of the pharmacological agent or cessation of application of electrical energy, and the subject is permitted to mount a compensatory response. In this following period, no additional stimulus is administered to the subject. The duration of this period between stimulus application, which may be referred to as a "holiday" period, may vary, but in representative embodiments is 1 day or longer, such as 2 days or longer, including 5 days or longer, 10 days or longer, e.g., 15 days or longer. As such, embodiments of the methods include non-chronic (i.e., non-continuous) application of the stimulus, e.g., non-chronic administration of a pharmacologic agent.

In certain embodiments, the methods include close monitoring or supervision of the subject during and/or after application of the stimulus. This monitoring may be completely automated, or at least in part performed manually, e.g., by a health care professional. For example, a health care professional can closely watch the subject following application of the stimulus as well as during the holiday period following stimulus application, and based on this monitoring determine when a next stimulus should be applied. Monitoring also assures that the symptom enhancement is not so severe as to be ultimately damaging to the subject at an unacceptable level. Certain aspects of the monitoring may be automated. For example, following administration, the subject may enter one or more physiological parameters into an automated system, which uses the input parameters to automatically determine whether the subject is staying within a predetermined set of physiological parameters, or whether intervention is necessary. In certain embodiments, the automated monitoring system may also be integrated with a stimulus application device, such that the system, based on monitored parameters, determines when next to administer a stimulus, the duration of the next stimulus, etc. As such, the method may be characterized as applying a first stimulus to the subject and monitoring the subject for a response thereto. Following this first step, the method further includes applying at least a second stimulus to the subject, wherein the second stimulus is determined based on the monitored response to the first stimulus.

In certain embodiments, wherein a decrease in the sympathetic/parasympathetic activity ratio is ultimately desired, the sympathetic/parasympathetic activity ratio is initially increased by applying a stimulus, followed by removal of the stimulus to allow for a compensatory decrease in sympathetic/parasympathetic activity ratio.

In certain embodiments, stimulus to the subject is done in an "irregularly irregular" manner. As such, duration of the stimulus application events, as well as duration of holiday periods between such events, varies randomly over the entire course of a treatment, or at least a portion thereof. In addition, the variation does not follow any pattern, but instead is random.

In practicing the subject methods, the applied stimulus may vary, where in certain embodiments the stimulus may be a pharmacological stimulus and/or an electrical stimulus. As such, in certain embodiments, the stimulus is a pharmacological stimulus. In other embodiments, the stimulus is an electrical stimulus. In yet other embodiments, the stimulus is a combination of pharmacological and electrical stimuli. Accordingly, in certain embodiments, the enhancing is by administering a pharmacological agent to the subject. In yet other embodiments, the enhancing is by electrical stimulation, e.g., by employing an implanted electrical energy application device.

Homeostatic Function Restoration

As summarized above, embodiments of the invention include at least partially restoring homeostatic function of the subject's neuroendocrine system in a manner sufficient to improve the condition in the subject. In certain embodiments, the subject methods are used to improve a condition in a subject by at least partially restoring the neuroendocrine homeostatic function, i.e., the ability control homeostasis, of one or more of the subjects' central nervous system endocrine glands. In particular instances, the method involves at least partially restoring the homeostatic function of the subject's hypothalamus. In other instances, the method involves at least partially restoring the homeostatic function of the subject's pituitary gland. In yet other embodiments, the method involves at least partially restoring the homeostatic function of the subject's pineal gland. As summarized above, certain embodiments of the methods include administering to the subject an amount of an apoptosis modulator effective to at least partially restore the target neuroendocrine homeostatic function. Yet other embodiments of the methods include restoring central nervous system endocrine gland function using protocols as described in U.S. patent application Ser. No. 61/834,772 and Ser. No. 14/303,492, the disclosures of which are herein incorporated by reference.

In certain embodiments, the target endocrine gland is the hypothalamus. The hypothalamus is a portion of the brain that is located below the thalamus and above the brain stem that functions to maintain homeostasis in a subject. In a subject, factors such as blood pressure, body temperature, fluid and electrolyte balance and body weight are held to a precise value called the set-point. Although this set-point can migrate over time, from day to day the hypothalamus functions to keep the set point of these factors fixed through homeostasis. To achieve homeostasis, the hypothalamus receives inputs about the state of these factors (e.g., information from vagus, spinal cord, retina, and limbic and olfactory systems) and, based on these inputs, sends neural signals to the autonomic system or endocrine signals to the pituitary. As such, the hypothalamus functions to maintain homeostasis through its control of the autonomic nervous system and endocrine system.

With respect to its endocrine function, the hypothalamus functions in controlling the pituitary gland, which in turn regulates various endocrine glands and organs. Such control of the pituitary gland occurs through two axes: 1) the hypothalamic-adenohypophyseal (anterior pituitary) axis; and 2) the hypothalamic-neurohypophyseal (posterior pituitary) axis. In some embodiments, the condition is improved by restoring hypothalamic endocrine function so that it is closer to that of a healthy human 25 year old.

In certain instances, the condition is improved by restoring hypothalamic function in the hypothalamic-adenohypophyseal (anterior pituitary) axis. In the hypothalamic-adenohypophyseal axis, hypophysiotropic hormones are released from the median eminence, itself a prolongation of the hypothalamus, into the hypophyseal portal system, which leads them to the anterior pituitary where they exert their regulatory functions on the secretion of adenohypopyseal hormones. As such, in certain instances, the subject methods are employed to treat a condition that is improved by restoring the function of the subject's hypothalamus to synthesize and/or secrete such hypophysiotropic hormones. Examples of hypophysiotropic hormones created and secreted by the hypothalamus in the hypothalamic-adenohypophyseal (anterior pituitary) axis include, but are not limited to: thyrotropin-releasing hormone (TRH, TRF, or PRH); corticotropin-releasing hormone (CRH or CRF); dopamine (DA or PIH); growth hormone-releasing hormone (GHRH); Gonadotropin-releasing hormone (GnRH or LHRH); somatostatin (SS, GHIH, or SRIF); vasopressin; oxytocin; neurotensin; or orexin.

In certain embodiments, the condition is improved by restoring hypothalamic function in the hypothalamic-neurohypophyseal (posterior pituitary) axis. In the hypothalamic-neurohypophyseal axis, neurohypophysial hormones are released from the posterior pituitary, which is a prolongation of the hypothalamus, into the circulation. In certain embodiments, the subject methods are employed to treat a condition that is improved by restoring the function of the subject's hypothalamus to synthesize and/or secrete such neurophypophysial hormones. Examples of neurohypophysial hormones created and secreted by the hypothalamus include, but are not limited to oxytocin and vasopressin.

In some instances, the subject methods are employed to improve a condition that can be improved by partially restoring the endocrine function of the subject's pituitary gland. The pituitary gland is a central nervous system endocrine gland that is regulated by the hypothalamus and is capable of secreting several different hormones that regulate homeostasis. In specific instances, the methods include partially restoring the ability of the pituitary gland to synthesize and/or secrete one or more specific hormones. The anterior pituitary synthesizes and secretes hormones under the influence of hypothalamic hormones through the hypothalamic-hypophsial portal system. Hormones synthesized and secreted by the anterior pituitary include somatotrophins (e.g., growth hormone); thyrotrophins (e.g., thyroid-stimulating hormone (TSH); corticotropins (e.g., adrenocorticotropic hormone (ACTH) and Beta-endorphin); lactotrophins (e.g., prolactic (PRL); gonadotropin (e.g., luteinizing hormone and follicle-stimulating hormone); and melanotrophin (e.g., melanocyte-stimulating hormone). Hormones stored and secreted by the posterior pituitary include oxytocin and vasopressin (antidiuretic hormone (ADH)). In some instances, the methods include partially restoring the ability of the anterior pituitary gland to synthesize and/or secrete one or more specific anterior pituitary hormones.

In other instances, the subject methods are employed to improve a condition that can be improved by partially restoring the endocrine function of the subject's pineal gland. The pineal gland produces the serotonin derivate melatonin, a hormone that affects the modulation of wake/sleep patterns and seasonal functions. In certain instances, the condition is improved by restoring the ability of the pineal gland to produce melatonin. In other instances, the condition is improved by restoring the ability of the pineal gland to regulate the hypothalamus.

At least partial restoration of the neuroendocrine homeostatic function so that it is at least closer to that of a healthy human (e.g., a healthy human 25 year old) is achieved in embodiments of the invention by administering to the subject an effective amount of an apoptosis modulator. By "at least closer" is meant, in some instances, that the target endocrine function is restored to be 50% or more, e.g., 75% or more of the target function, such as 80% or more of the target function, including 90% or more of the target function, e.g., 95% or more of the target function, including 99% or more of the target function. Neuroendocrine homeostatic function can be assayed using any suitable method.

In some instances, at least partial restoration of the homeostatic function of the neuroendocrine system results in restoring the normal function of the autonomic function of one or more central nervous system endocrine gland. In certain embodiments of the subject method, the restoration of the central nervous system endocrine function modulates autonomic function. By "modulating" is meant altering or changing one aspect or component to provide a change, alteration or shift in another aspect or component. Modulating autonomic function is achieved by modulating at least one portion of the subject's autonomic nervous system. By "modulating at least one portion of the subject's autonomic nervous system" is meant altering or changing at least a portion of an autonomic nervous system by a means to provide a change, alteration or shift in at least one component or aspect of the autonomic nervous system.

In some instances of the subject methods, modulation of the autonomic nervous system includes modulating the parasympathetic and/or sympathetic activity in the subject, e.g., as described above. As reviewed above, "parasympathetic activity" refers to activity of the parasympathetic nervous system whereas "sympathetic activity" refers to activity of the sympathetic nervous system. With respect to the hypothalamus, anterior and medial hypothalamic regions exert parasympathetic effects, whereas the posterior and lateral hypothalamic regions exert sympathetic effects. Stimulation of the anterior hypothalamus (anterolateral region) excites the parasympathetic nervous system and inhibits the sympathetic nervous system. Upon such stimulation, heart and blood pressures decrease (the vagal response), the visceral vessels dilate, peristalsis and secretion of digestive juices increase, the pupils constrict and salivation increases. In contrast, stimulation of the posterior hypothalamus (posteromedial region) excites the sympathetic nervous system and inhibits the parasympathetic nervous system. Upon such stimulation, heart beat and blood pressure increases, the visceral vessels constrict, peristalsis and secretion of gastric juices decrease, pupils dilate and sweating and piloerection occur.

In some embodiments, the restoration of neuroendocrine homeostatic function results in at least one of decreasing parasympathetic activity and/or increasing sympathetic activity in a subject to improve a condition caused by parasympathetic bias. In other embodiments, the restoration of the neuroendocrine homeostatic function results in at least one of decreasing sympathetic activity and/or increasing parasympathetic activity in a subject to improve a condition caused by sympathetic bias.

Restoration of homeostatic function of a central nervous system endocrine gland (e.g., hypothalamus) that also modulates the autonomic nervous system may be carried out using an apoptotic modulator, e.g., as described below. The neuroendocrine apoptotic modulation may provide an increase in function of at least a portion of the autonomic system, e.g., increase function in at least one sympathetic or parasympathetic nerve fiber, and/or provide a decrease in function or dampening of a portion of the autonomic system, e.g., may inhibit activity in at least one sympathetic or parasympathetic nerve fiber or inhibit nerve pulse transmission.

In some instances, the modulation that is achieved in practicing methods of the invention may be quantified. One way of quantifying modulation of at least one portion of the subject's autonomic nervous system is the parasympathetic/sympathetic activity ratio. By "parasympathetic/sympathetic activity ratio" is meant the ratio of activity of the sympathetic nervous system to the activity of the parasympathetic nervous system. As such, methods according to certain embodiments include modulating a sympathetic/parasympathetic activity ratio in the subject.

In some instances, the neuroendocrine gland (e.g., hypothalamus) homeostatic function is restored in such a manner to shift or change parasympathetic activity and/or sympathetic activity from a first state to a second state, where the second state is characterized by an increase or decrease in the sympathetic activity/parasympathetic activity ratio relative to the first state. Accordingly, some embodiments of the subject invention include restoring the normal homeostatic function of a central nervous system endocrine gland in such a manner that modulates at least a portion of a subject's autonomic nervous system to increase the sympathetic activity/parasympathetic activity ratio, i.e., to increase sympathetic activity relative to parasympathetic activity (in other words to decrease parasympathetic activity relative to sympathetic activity) so as to treat a subject for a condition that can be treated by such modulation (i.e. a condition caused by parasympathetic bias).

Other embodiments of the subject invention include restoring the homeostatic function of the neuroendocrine system in a manner sufficient to decrease the sympathetic activity/parasympathetic activity ratio, i.e., to decrease sympathetic activity relative to parasympathetic activity (in other words, to increase parasympathetic activity relative to sympathetic activity) so as to treat a subject for a condition that can be treated by such modulation (i.e. a condition caused by sympathetic bias).

As will be described in greater detail below, while the ratio of sympathetic function/parasympathetic function may be modulated according to embodiments of the subject invention to treat or improve a subject for a condition (e.g., aging associated conditions) the net result may be a parasympathetic bias (i.e., a parasympathetic dominance), a sympathetic bias (i.e., sympathetic dominance), or the activities of the sympathetic system and parasympathetic system may be substantially equal (i.e., neither is dominant).

By "bias", is meant that the particular "biased" component of the autonomic nervous system has a higher activity level than the other component. For example, a parasympathetic bias refers to a higher level of parasympathetic activity than sympathetic activity, and vice versa, where such bias may be systemic or localized. As such, by "vagal bias", is meant that that the particular biased component of the autonomic nervous system that has a higher activity level than the other component is the vagus nerve or a portion of the autonomic nervous system associated with the vagus nerve. Vagal bias may be characterized by one or more of vagal dominance, vagal hypersensitivity and/or sympathetic insufficiency. The net result of the subject methods to treat a condition may be higher or greater sympathetic activity relative to parasympathetic activity in at least the area of the targeted autonomic system (i.e., that portion in need of modulation), or substantially equal activity levels of sympathetic activity and parasympathetic activity.

Further details regarding modulation of autonomic function and conditions treatable thereby are provided in U.S. patent application Ser. No. 61/834,772 and Ser. No. 14/303,492, the disclosures of which are herein incorporated by reference.

In certain embodiments of the subject methods, at least partially restoring homeostatic function of the subject's neuroendocrine system is achieved using an apoptosis modulator. Apoptosis modulators employed in methods of the invention are active agents that, upon administration to a subject, result in a change, e.g., decrease or increase, in the occurrence of cellular apoptosis in a least a portion of subject's neuroendocrine system. The term "apoptosis" is employed herein in its conventional sense to refer to programmed cell death.

In some instances, the apoptosis modulator that is administered to the subject is an apoptosis inhibitor. Any convenient apoptosis inhibitor may be employed, wherein the apoptosis inhibitor may exhibit inhibitory activity on an extrinsic apoptotic pathway, an intrinsic apoptotic pathway, or a general apoptotic pathway. Extrinsic apoptotic pathway factors that may be targeted by the apoptotic inhibitor include, but are not limited to: A20, CYLD, APO2L, Bid, Caspase-3, Caspase-7, Caspase-8, CD95L, c-IAP1, c-IAP2, DDR4/5, DR/CD95, FADD, FLIP, ITCH, RIP2, TNF-alpha, TNFR1, TRADD, TRAF2, TRAIL and the like. Intrinsic apoptotic pathway factors that may be targeted by the apoptotic inhibitor include, but are not limited to: Apaf-1, BAD, BAK, BAX, BCL-2, BCL-XL, BIM, Caspase-9, Cytochrome C, FBW7, MCL1, ML-IAP, MULE, NOXA, p53, PUMA, SMAC, tBid, tBID, USP9X, XIAP and the like. General apoptotic pathway factors that may be targeted by the apoptotic inhibitor include, but are not limited to: AIF, AKT/PKT, ANT, APAF1, APO3L, ARTS, ASK1, ATM, BAGs, BCL-X, BI-1, BIT1, CAD, Calpains, Caspase-10, Caspase-12, CHK2 CYPD, DAXX, DNA-PK (Ku70), EndoG, FAS, FASL, HSP70, HSP90, HTRA2/OMI, Humanin, ICAD, IKK, IRE-alpha, MDM2, MMP, NUR77/TR3, p19ARF, p53AIP1, PAR4, PARP, PBR, PI3K, PIDD, PKC, PML, PTEN, R90RSK, Survivin, TNF, TRAILR1, TRAILR2, VDAC, ZIPK and the like. In some instances, the apoptosis inhibitor is not a caspase inhibitor.

Depending on the particular embodiments being practiced, a variety of different types of active agents may be employed. In some instances, the agent modulates the activity of the protein following expression, such that the agent is one that changes the activity of the protein encoded by a target gene following expression of the protein from the target gene. In these instances, the agent is one that may act directly with protein encoded by the target gene. In these instances, the agent may be one that selectively reduces the deleterious, e.g., apoptotic, activity of the encoded protein. In certain embodiments, such agents are inhibitors of apoptotic activity of a target protein.

In yet other embodiments, the agent modulates expression of the RNA and/or protein from the gene, such that it changes the expression of the RNA or protein from the target gene in some manner. In these instances, the agent may change expression of the RNA or protein in a number of different ways. In certain embodiments, the agent is one that reduces, including inhibits, expression of a functional target protein. Inhibition of protein expression may be accomplished using any convenient means, including use of an agent that inhibits protein expression, such as, but not limited to: antisense agents, RNAi agents, agents that interfere with transcription factor binding to a promoter sequence of the target gene, or inactivation of the target gene, e.g., through recombinant techniques, etc.

For example, antisense molecules can be used to down-regulate expression of a target gene in the cell. The antisense reagent may be antisense oligodeoxynucleotides (ODN), particularly synthetic ODN having chemical modifications from native nucleic acids, or nucleic acid constructs that express such anti-sense molecules as RNA. The antisense sequence is complementary to the mRNA of the targeted protein, and inhibits expression of the targeted protein. Antisense molecules inhibit gene expression through various mechanisms, e.g., by reducing the amount of mRNA available for translation, through activation of RNAse H, or steric hindrance. One or a combination of antisense molecules may be administered, where a combination may include multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), Nature Biotechnol. 14:840-844).

A specific region or regions of the endogenous sense strand mRNA sequence is chosen to be complemented by the antisense sequence. Selection of a specific sequence for the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Oligonucleotides may be chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine.

5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434-42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43-56.

In addition, the transcription level of a target protein can be regulated by gene silencing using RNAi agents, e.g., double-strand RNA (Sharp (1999) *Genes and Development* 13: 139-141). RNAi, such as double-stranded RNA interference (dsRNAi) or small interfering RNA (siRNA), has been extensively documented in the nematode *C. elegans* (Fire, A., et al, *Nature,* 391, 806-811, 1998) and routinely used to "knock down" genes in various systems. RNAi agents may be dsRNA or a transcriptional template of the interfering ribonucleic acid which can be used to produce dsRNA in a cell. In these embodiments, the transcriptional template may be a DNA that encodes the interfering ribonucleic acid. Methods and procedures associated with RNAi are also described in WO 03/010180 and WO 01/68836, all of which are incorporated herein by reference. dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enables one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety). A number of options can be utilized to deliver the dsRNA into a cell or population of cells such as in a cell culture, tissue, organ or embryo. For instance, RNA can be directly introduced intracellularly. Various physical methods are generally utilized in such instances, such as administration by microinjection (see, e.g., Zernicka-Goetz, et al. (1997) Development 124:1133-1137; and Wianny, et al. (1998) Chromosoma 107: 430-439). Other options for cellular delivery include permeabilizing the cell membrane and electroporation in the presence of the dsRNA, liposome-mediated transfection, or transfection using chemicals such as calcium phosphate. A number of established gene therapy techniques can also be utilized to introduce the dsRNA into a cell. By introducing a viral construct within a viral particle, for instance, one can achieve efficient introduction of an expression construct into the cell and transcription of the RNA encoded by the construct.

In another embodiment, the target gene is inactivated so that it no longer expresses a functional protein. By inactivated is meant that the gene, e.g., coding sequence and/or regulatory elements thereof, is genetically modified so that it no longer expresses a functional target protein. The alteration or mutation may take a number of different forms, e.g., through deletion of one or more nucleotide residues, through exchange of one or more nucleotide residues, and the like. One means of making such alterations in the coding sequence is by homologous recombination. Methods for generating targeted gene modifications through homologous recombination are known in the art, including those described in: U.S. Pat. Nos. 6,074,853; 5,998,209; 5,998,144; 5,948,653; 5,925,544; 5,830,698; 5,780,296; 5,776,744; 5,721,367; 5,614,396; 5,612,205; the disclosures of which are herein incorporated by reference.

Also of interest in certain embodiments are dominant negative mutants of target proteins, where expression of such mutants in the cell result in a modulation, e.g., decrease, in target protein activity. Dominant negative mutants are mutant proteins that exhibit dominant negative target protein activity. As used herein, the term "dominant negative activity" refers to the inhibition, negation, or diminution of certain particular activities of a target protein, such as the apoptotic activity of a target protein. Dominant negative mutations are readily generated for corresponding proteins. These may act by several different mechanisms, including mutations in a substrate-binding domain; mutations in a catalytic domain; mutations in a protein binding domain (e.g. multimer forming, effector, or activating protein binding domains); mutations in cellular localization domain, etc. A mutant polypeptide may interact with wild-type polypeptides (made from the other allele) and form a non-functional multimer. In certain embodiments, the mutant polypeptide will be overproduced. Point mutations are made that have such an effect. In addition, fusion of different polypeptides of various lengths to the terminus of a protein, or deletion of specific domains can yield dominant negative mutants. General strategies are available for making dominant negative mutants (see for example, Herskowitz (1987) Nature 329:219, and the references cited above). Such techniques are used to create loss of function mutations, which are useful for determining protein function. Methods that are well known to those skilled in the art can be used to construct expression vectors containing coding sequences and appropriate transcriptional and translational control signals for increased expression of an exogenous gene introduced into a cell. These methods include, for example, in vitro recombinant DNA techniques, synthetic techniques, and in vivo genetic recombination. Alternatively, RNA capable of encoding gene product sequences may be chemically synthesized using, for example, synthesizers. See, for example, the techniques described in "Oligonucleotide Synthesis", 1984, Gait, M. J. ed., IRL Press, Oxford.

In yet other embodiments, the agent is an agent that modulates, e.g., inhibits, target protein activity by binding to the target protein and/or inhibiting binding of target protein to a second protein. For example, small molecules that bind to a target protein and inhibit its activity are of interest. Naturally occurring or synthetic small molecule compounds of interest include numerous chemical classes, such as organic molecules, e.g., small organic compounds having a molecular weight of more than 50 and less than about 2,500 daltons. Candidate agents comprise functional groups for structural interaction with proteins, particularly hydrogen bonding, and typically include at least an amine, carbonyl, hydroxyl or carboxyl group, preferably at least two of the functional chemical groups. The candidate agents may include cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof. Such molecules may be identified, among other ways, by employing the screening protocols described below.

In some instances the agent is an inhibitor of Caspase activity, i.e. a Caspase inhibitor. Caspase inhibitors that may be employed include, but are not limited to: AQZs, nicotinyl aspartyl ketones, M826, M867, IDN-6556, Ac-AAVALL-PAVLLALLAPDEVD-CHO (Ac-Ala-Ala-Val-Ala-Leu-Leu-Pro-Ala-Val-Leu-Leu-Ala-Leu-Leu-Ala-Pro-Asp-Glu-Val-Asp-cho), Ac-AAVALLPAVLLALLAPLEHD-CHO (Ac-Ala-Ala-Val-Ala-Leu-Leu-Pro-Ala-Val-Leu-Leu-Ala-Leu-Leu-Ala-Pro-Leu-Glu-His-Asp-CHO), Ac-AAVALL-PAVLLALLAPLEVD-CHO (Ac-Ala-Ala-Val-Ala-Leu-Leu-Pro-Ala-Val-Leu-Leu-Ala-Leu-Leu-Ala-Pro-Leu-Glu-Val-Asp-cho), Ac-DEVD-CHO (Ac-Asp-Glu-Val-Asp-Cho), Ac-DEVD-CMK (Ac-Asp-Glu-Val-Asp-Chloromethylketone), Ac-IEFD-CHO (Ac-Ile-Glu-Phe-Asp-cho), Ac-LEHD-CMK (Ac-Leu-Glu-His-Asp Chloromethylketone), Ac-LEVD-CHO (Ac-Leu-Glu-Val-Asp-cho), Ac-VAD-CHO (Ac-Val-Ala-Asp-cho), Ac-VEID-FMK (Ac-Val-Glu-Ile-Asp fluoromethylketone), Ac-YVAD-AOM (Ac-Tyr-Val-Ala-Asp-2,6-dimethylbenzoyloxymethyl ketone), Ac-YVAD-CHO (Ac-Tyr-Val-Ala-Asp-cho), Ac-YVAD-CMK (Ac-Tyr-Val-Ala-Asp-Chloromethylketone), BI-9B12 (Benzo[b]1,4-dioxane), Biotin-FA-FMK (Biotin-Phe-Ala-Fluoromethylketone), Biotin-VAD-FMK (Biotin-Val-Ala-Asp-Fluoromethylketone), Boc-D-FMK (Boc-Asp(OMe)-fluoromethyl ketone), caspase-1 inhibitor (Ac-Ala-Ala-Val-Ala-Leu-Leu-Pro-Ala-Val-Leu-Leu-Ala-Leu-Leu-Pro-Tyr-Val-Ala-Asp-cho), caspase-1 substrate (Asn-Glu-Ala-Tyr-Val-His-Asp-Ala-Pro-Val-Arg-Ser-Leu-Asn), DICA (2-(2,4-Dichloro-phenoxy)-n-(2-mercapto-ethyl)-acetamide), Geranylgeraniol (all trans-3,7,11-15-Tetramethyl -2,6,10,14-hexadecatetraen-1-ol), Gly-Phe beta-naphthylamide (Glycylphenylalanine 2-naphthylamide), Isatin Sulfonamide 16 (5-[(S)-(+)-2-(Methoxymethyl) pyrrolidino]sulfonylisatin), Ivachtin (2-[4-Methyl-8-(morpholin-4-ylsulfon yl)-1,3-dioxo-1,3-dihydro-2H-pyrrolo[3, 4-c]quinolin-2-yl]ethyl acetate), L-709049 (N-Ac-Tyr-Val-Ala-Asp-CHO), M50054 (2,2'-Methylenebis(1,3-cyclohexanedione)), Necrostatin-5 ({[3-(4-methoxyphenyl)-4-oxo-3,4,5,6,7,8-hexahydro[1] benzothieno[2,3-d]pyrimidin-2-yl]sulfanyl}acetonitrile), NSCI (1-(4-Methoxybenzyl)-5-[2-(pyridin-3-yl-oxymethyl) pyrrolidine-1-sulfonyl]-1H-indole-2,3-dione), PAO (Phenylarsine Oxide), PKR Inhibitor ((8Z)-8-(1H-imidazol-5-ylmethylidene)-6H-pyrrolo[2,3-g][1,3]benzothiazol-7-one), Q-VD-OPH (N-(2-Quinolyl)-L-valyl-L-aspartyl-(2,6-difluorophenoxy) methylketone), Wedelolactone (1,8,9-Trihydroxy-3-methoxy-6H-benzofuro[3,2-c][1]benzopyran-6-one), Z-Asp-CH2-DCB (Z-Asp-2,6-dichlorobenzoyloxymethylketone), Z-DEVD-FMK (Z-Asp (OMe)-Glu(OMe)-Val-Asp(OMe) fluoromethylketone), Z-FA-FMK (Z-Phe-Ala fluoromethyl ketone), Z-FA-FMK (Z-Phe-Ala fluoromethyl ketone), Z-IETD-FMK (Z-Ile-Glu-Thr-Asp fluoromethylketone), Z-LEHD-FMK (Z-Leu-Glu-His-Asp fluoromethylketone), Z-VAD(OH)-FMK (Z-Val-Ala-Asp(OH) fluoromethylketone), Z-VAD(OMe)-FMK (Z-Val-Ala-Asp(OMe) fluoromethylketone), Z-VAD-FMK (Z-Val-Ala-Asp(OMe)-fluoromethylketone), Z-VDVAD-FMK (Z-Val-Asp-Val-Ala-Asp-fluoromethylketone), Z-VE (OMe)ID(OMe)-FMK (Z-Val-Glu(OMe)-Ile-Asp(OMe) fluoromethylketone), Z-WEHD-FMK (Z-Trp-Glu-His-Asp fluoromethylketone), Z-YVAD-FMK (Z-Tyr-Val-Ala-Asp-fluoromethylketone) and the like.

In still other embodiments, the agent is a modulator of a non-caspase member of the apoptotic pathway. Modulators including e.g, antibodies, peptides, small molecules, and the like. Modulators that may be employed include, but are not limited to: modulators of death receptors or death receptor complex components (e.g., TRAIL, HGS-ETR1, HGS-TR2J, C75, EGCG, cerulenin, and the like), modulators of FLIP (e.g., CDDO, and the like), modulators of IKK (e.g., SPC-839, SC-514, a pyridooxazinone derivative, BMS-345541, beta-carboline, a 2-amino-6-[2-cyclopropylmethoxy)-6-hydrophenyl]-4-piperidin-4-ylnicotinonitrile, an ureido-thiophene carboxamide derivative, an indole carboxamide derivative, a benzo-imidazole carboxamide derivative, an amino-imidazole carboxamide derivative, a pyridyl cyanoguanidine derivative, an aniline-pyrimidine derivative, and the like), modulators of AKT/PKB (e.g., DPIs, 1 L-6hydroxymethyl-chiro-inositol 2(R)-2-O-methyl-3-O-octadecylcarbonate, API-2, and the like), modulators of PI3K (e.g., wortmannin, LY294002, PX866, and the like), modulators of HSP90 (e.g., geldanamycin, PU24FCI, and the like), modulators of BID (4-phenylsulphanyl-phenylamine derivatives and the like), modulators of IAP (e.g., benzenesulfonamide derivatives, capped tripeptides containing unnatural amino acids, embeline, di/triphenylureas, compound 3, and the like), modulators of BAX (e.g., humanin peptides, 3,6-dibromocarbazole piperazine derivatives of 2-propanol, Ku70 peptides, and the like), modulators of BCL-2 (e.g., HA14-1 analogues, CPM-1285 analogues, BH3I-1, BH3I-2, antimycin A3, compound 6, a terphenyl derivative, apogossypol, theaflavin, SAHBs, A-779024, and the like), modulators of p53 (e.g., pifithrin-alpha, CP-31398, and the like), modulators of NUR77/TR3 (e.g., 3C1-AHPC/ MM11453 and the like), modulators of HSP70 (e.g., ADD70 and the like), modulators of 26S proteasome degradation (MG-115, MG-132, bortezomib, epoxomincin, and the like), modulators of the PML/PAR4/ZIPK/DAXX complex (e.g., arsenicals, interferon, and the like), modulators of p53 responsive genes survivin and BCL-2 (e.g., survivin antisense, genasense, and the like), modulators of NF-kappa-B responsive genes (e.g., XIAP antisense), modulators of PARP (e.g., INO-1001, FR255595, 3-AB, NU1025, AG14361, INH2BP, GPI6150, PJ34, and the like), modulators of MDM2 (e.g., chlorofusin, sulfonamide compound 1, 2-phenoxybenzoyl-tryptophan derivatives, nutlins, and the like) and the like.

In other embodiments the agent is an inhibitor of the general apoptotic pathway, i.e. an apoptosis inhibitor. Apoptosis inhibitors that may be employed include, but are not limited to: 10058-F4 (5-[(4-Ethylphenyl)methylene]-2-thioxo-4-thiazolidinone), 4'-Methoxyflavone (2-(4-Methoxyphenyl)-4H-chromen-4-one), BAX Inhibiting Peptide V5 (Val-Pro-Met-Leu-Lys), BEPP monohydrochloride (1H-Benzimidazole-1-ethanol, 2,3-dihydro-2-imino-alpha-(phenoxymethyl)-3-(phenylmethyl)-monohydrochloride), BI-6C9 (N-[4-[(4-Aminophenyl)thio]phenyl]-4-[[(4-methoxyphenyl)sulfonyl]amino]-Butanamide), Bongkrekic acid ((2E,4E,6R,8E,10E,14E,17S,18E,20E)-20-(carboxymethyl)-6-methoxy-2,5,17-trimethyldocosa-2,4,8,10,14,18, 20-heptaenedioic acid), BTZO-1 (2-Pyridin-2-yl-4H-1,3-benzothiazin-4-one), Calpeptin (N-Benzyloxycarbonyl-L- leucylnorieucinal), Clofarabine ((2R,3R,4S,5R)-5-(6-amino-2-chloropurin-9-yl)-4-fluoro-2-(hydroxymethyl) oxolan-3-ol), Combretastatin A4 (1-(3,4,5-Trimethoxyphenyl)-2-(3'-hydroxy-4'-methoxyphenyl) ethane 3,4,5-trimethoxy-3'-hydroxy-4'-methoxystilbene), CTP Inhibitor (4-Chloro-3-[[(3-nitrophenyl)amino]sulfonyl]-benzoic acid), Cyclic Pifithrin-α hydrobromide (2-(4-Methylphenyl)imidazo[2,1-b]-5,6,7,8-tetrahydrobenzothiazole hydrobromide), EM20-25 (5-(6-Chloro-2,4-dioxo-1,3,4,10-tetrahydro-2H-9-oxa-1,3-diaza-anthracen-10-yl)-pyrimidine-2,4,6-trione), Fasentin (N-[4-Chloro-3-(trifluoromethyl)phenyl]-3-oxobutanamide), GNF-2 (3-[6-[[4-(Trifluoromethoxy)phenyl]amino]-4-pyrimidinyl] benzamide), IM-54 (1-Methyl-3-(1-methyl-1-indol-3-yl)-4-(pentylamino)-1H-pyrrole-2,5-dione), Mdivi-1 (3-(2,4-Dichloro-5-methoxyphenyl)-2,3-dihydro-2-thioxo-4(1H)-quinazolinone), MDL 28170 (Calpain Inhibitor III), Mitochondrial Fusion Promoter M1 ((E)-4-Chloro-2-(1-(2-(2,4,6-trichlorophenyl)hydrazono)ethyl)phenol), Necrostatin-1 (5-(1H-Indol-3-ylmethyl)-3-methyl-2-thioxo-4-Imidazolidinone), NEM (N-Ethylmaleimide), NS3694 (4-Chloro-2-[3-(3-trifluoromethyl-phenyl)-ureido]benzoic acid), Oridonin (7a,20-Epoxy-1a,6b,7,14-tetrahydroxy-Kaur-16-en-15-one, Isodonol), PD 151746 (3-(5-Fluoro-1H-indol-3-yl)-2-mercapto-2-propenoic acid), PDI inhibitor 16F16 (2-(2-Chloroacetyl)-2,3,4,9-tetrahydro-1-methyl-1H-pyrido[3,4-b]indole-1-carboxylic acid methyl ester), Pentostatin ((8R)-3-(2-Deoxy-(3-D-erythro-pentofuranosyl)-3,4,7,8-tetrahydroimidazo[4,5-d][1,3]diazepin-8-ol, 2'-dCF), Pifithrin-alpha (2-(2-Imino-4,5,6,7-tetrahydrobenzothiazol-3-yl)-1-p-tolylethanone hydrobromide), Pifithrin-mu (2-Phenylethynesulfonamide), Piperlongumine (5,6-Dihydro-1-(1-oxo-3-[3,4,5-trimethoxyphenyl]-trans-2-propenyl)-2[1H]-pyridinone), R18 trifluoroacetate (Pro-His-Cys-Val-Pro-Arg-Asp-Leu-Ser-Trp-Leu-Asp-Leu-Glu-Ala-Asn-Met-Cys-Leu-Pro trifluoroacetate), recombinant BAG1 (BCL2-associated athanogene), S-15176 difumarate salt (N-[(3,5-Di-tert-butyl-4-hydroxy-1-thiophenyl)]-3-propyl-N'-(2,3,4-trimethoxybenzyl)piperazine difumarate salt) and the like.

In some instances, the active agent is configured to selectively target neuroendocrine cells. For example, the active agent may be conjugated to a neuroendocrine target moiety. Such target moieties may include markers of neuroendocrine tissues or agents that bind neuroendocrine markers. Naturally occurring and synthetic neuroendocrine markers and agents that bind neuroendocrine markers are of interest. Agents that bind neuroendocrine markers may, for example, include antibodies, peptides, or small molecules that bind neuroendocrine markers.

In some embodiments, neuroendocrine markers that may be employed to selectively target neuroendocrine cells include markers of intermediate filaments. Intermediate filament markers useful for selectively targeting neuroendocrine cells include, but are not limited to: cytokeratins (CK), CAM 5.2 (CK8 and CK18), MNF116 (CK5, CK6, CK8, CK17, and CK19), CK20, neurofilaments, neurofilament triplet proteins, peripherin, Nf-66/alphainternexin and the like.

In yet other embodiments, neuroendocrine markers that may be employed to selectively target neuroendocrine cells include markers of enzymes present in neuroendocrine cells. Neuroendocrine enzyme markers useful for selectively targeting neuroendocrine cells include, but are not limited to: neuron-specific enolase (protein 14-3-2), endopeptidases, prohormone convertases (PC1/PC3, PC2), carboxypeptidases, carboxypeptidase H, carboxypeptidase E, peptidyl-glycine alpha amidating mono-oxygenase (PAM), peptidylglycine alpha hydroxylating mono-oxygenase, peptidylglycine-alpha-hydroxylysine alpha amidating lyase and the like.

In some other instances, neuroendocrine markers that may be employed to selectively target neuroendocrine cells include markers of hormones, hormone precursors, or hormone derivatives present in neuroendocrine cells. Neuroendocrine hormone markers useful for selectively targeting neuroendocrine cells include, but are not limited to: somatostatin, calcitonin, insulin, gastrin, ACTH (AdrenoCorticotropic Hormone or Corticotropin), TSH (Thyroid-Stimulating Hormone or Thyrotropin), PRL (Prolactin or Luteotropic hormone (LTH), GH (Growth Hormone), FSH (Follicle-Stimulating Hormone), LH (Luteinizing Hormone), Oxytocin, ADH (AntiDiuretic Hormone or Vasopressin), HCG (Human Chorionic Gonadopropin), Testosterone, Estradiol, Antimullerian Hormone, Progesterone, Inhibin B, Activin and the like.

In yet other embodiments, neuroendocrine markers that may be employed to selectively target neuroendocrine cells include markers of secretory granule proteins and peptides derived from the proteolytic cleavage of secretory granule proteins present in neuroendocrine cells. Neuroendocrine secretory granule protein markers useful for selectively targeting neuroendocrine cells include, but are not limited to: chromogranins, chromogranin A, chromogranin B, secretogranins, secretogranin II, pancreastatin, parastatin, vasostatin, chromostatin, beta granin, HISL-9 antibody, PHE5 antibody and the like.

In still further instances, neuroendocrine markers that may be employed to selectively target neuroendocrine cells include general markers of neuroendocrine cells. General neuroendocrine markers useful for selectively targeting neuroendocrine cells include, but are not limited to: synaptophysin, synaptic vesicle protein 2 (SV2), neural cell adhesion molecules (NCAMs), CD56, 123C3 antibody, CD57, CD99, thyroid transcription factor-1 (TTF-1), synaptobrevin, synaptotagmin, SNAP-25. SNAP receptor (SNARE), syntaxin, Rab3A, neurone-specific enolase, Protein Gene Product 9.5 (PGP 9.5) and the like.

In some instances, the active agent is configured to cross the blood brain barrier. For example, the active agent may be conjugated to a moiety that confers upon the active agent the ability to cross the blood brain barrier. Such a configuration allows for the targeting of the active agent to tissues within the blood brain barrier. In some embodiments the subject moiety may be a peptide, e.g., a cell-penetrating peptide. Suitable peptides that facilitate crossing of the blood brain barrier include, but are not limited to positively charged peptides with amphipathic characteristics, such as MAP, pAntp, Transportan, SBP, FBP, $TAT_{48-60}$, SynB1, SynB3 and the like.

In other embodiments, the subject moiety may be a polymer. Suitable polymers that facilitate crossing of the blood brain barrier include, but are not limited to, surfactants such as polysorbate (e.g., Tween® 20, 40, 60 and 80); poloxamers such as Pluronic® F 68; and the like. In some embodiments, an active agent is conjugated to a polysorbate such as, e.g., Tween® 80 (which is Polyoxyethylene-80-sorbitan monooleate), Tween® 40 (which is Polyoxyethylene sorbitan monopalmitate); Tween® 60 (which is Polyoxyethylene sorbitan monostearate); Tween® 20 (which is Polyoxyethylene-20-sorbitan monolaurate); polyoxyethylene 20 sorbitan monopalmitate; polyoxyethylene 20 sorbitan monostearate; polyoxyethylene 20 sorbitan monooleate; etc. Also suitable for use are water soluble polymers, including, e.g.: polyether, for example, polyalkylene oxides such as polyethylene glycol ("PEG"), polyethylene oxide ("PEO"), polyethylene oxide-co-polypropylene oxide ("PPO"), co-polyethylene oxide block or random copolymers, and poly-vinyl alcohol ("PVA"); poly(vinyl pyrrolidinone) ("PVP"); poly(amino acids); dextran, and proteins such as albumin. Block co-polymers are suitable for use, e.g., a polyethylene oxide-polypropylene oxide-polyethylene-oxide (PEO-PPO-PEO) triblock co-polymer (e.g., Pluronic® F68); and the like; see, e.g., U.S. Pat. No. 6,923,986. Other methods for crossing the blood brain barrier are discussed in various publications, including, e.g., Chen & Liu (2012) Advanced Drug Delivery Reviews 64:640-665.

The targeting moiety may be attached to the subject active agent via any convenient method. The targeting moiety may be attached to the active agent via a single bond or a suitable linker, e.g., a PEG linker, a peptidic linker including one or more amino acids, or a saturated hydrocarbon linker. A variety of linkers find use in the subject modified compounds.

In certain embodiments where targeting moieties or active agents are small molecule compounds, such compounds may contain, or be modified to contain, an α-nucleophilic group that serves as a reactive partner useful in conjugation to a compound disclosed herein. General methods are known in the art for chemical synthetic schemes and conditions useful for synthesizing a compound of interest (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

In certain embodiments where targeting moieties or active agents are peptides, any convenient reagents and methods may be used to conjugate the targeting moiety and subject active agent, for example, conjugation methods as described in G. T. Hermanson, "Bioconjugate Techniques" Academic Press, 2nd Ed., 2008, solid phase peptide synthesis methods, or fusion protein expression methods. Reactive functional groups for conjugation of peptidic compounds, via an optional linker, include, but are not limited to: an azido group, an alkynyl group, a phosphine group, a cysteine residue, a C-terminal thioester, aryl azides, maleimides, carbodiimides, N-hydroxysuccinimide (NHS)-esters, hydrazides, PFP-esters, hydroxymethyl phosphines, psoralens, imidoesters, pyridyl disulfides, isocyanates, aminooxy-, aldehyde, keto, chloroacetyl, bromoacetyl, and vinyl sulfones.

Other variations of standard peptide coupling chemistry may be employed. Examples of peptide coupling reagents that can be used include, but are not limited to, DCC (dicyclohexylcarbodiimide), DIC (diisopropylcarbodiimide), di-p-toluoylcarbodiimide, BDP (1-benzotriazole diethylphosphate-1-cyclohexyl-3-(2-morpholinylethyl)carbodiimide), EDC (1-(3-dimethylaminopropyl-3-ethyl-carbodiimide hydrochloride), cyanuric fluoride, cyanuric chloride, TFFH (tetramethyl fluoroformamidinium hexafluorophosphosphate), DPPA (diphenylphosphorazidate), BOP (benzotriazol-1-yloxytris(dimethylamino)phosphonium hexafluorophosphate), HBTU (0-benzotriazol-1-yl-N,N,N',N'-tetramethyluronium hexafluorophosphate), TBTU (O-benzotriazol-1-yl-N,N,N',N'-tetramethyluronium tetrafluoroborate), TSTU (O—(N-succinimidyl)-N,N,N',N'-tetramethyluronium tetrafluoroborate), HATU (N-[(dimethylamino)-1-H-1,2,3-triazolo[4,5,6]-pyridin-1-ylmethylene]-N-methylmethanaminium hexafluorophosphate N-oxide), BOP-Cl (bis(2-oxo-3-oxazolidinyl)phosphinic chloride), PyBOP ((1-H-1,2,3-benzotriazol-1-yloxy)-tris(pyrrolidino) phosphonium tetrafluorophopsphate), BrOP (bromotris(dimethylamino)phosphonium hexafluorophosphate), DEPBT (3-(diethoxyphosphoryloxy)-1,2,3-benzotriazin-4(3H)-one) PyBrOP (bromotris(pyrrolidino)phosphonium hexafluorophosphate).

In certain embodiments where targeting moieties or active agents are oligonucleotides, any convenient reagents and methods may be used to conjugate the targeting moiety and subject active agent. For example conjugation methods described in P. Herdewijn, "Oligonucleotide Synthesis" Humana Press, 2005, such as total stepwise solid-phase synthesis methods, or methods utilizing incorporation of 2'-aldehydes for use in ligation via hydrazine, oxime, or thiazolidine linkages. In other cases, the oligonucleotide may be first conjugated, by methods well known in the art, to a natural or synthetic amino acid such that functional groups on the amino acid may be utilized for conjugation by any of the relevant peptide conjugation methods described herein.

In another embodiment where the targeting moiety is an antibody, the antibody may include a light chain polypeptide including a C-terminal amino acid extension, which extension includes a cysteine residue, where the agent is conjugated to the cysteine residue (directly or indirectly (e.g., via a linker)) of the C-terminal amino acid extension. In one embodiment, conjugation method involves the preferential (or "biased") conjugation of agent to the cysteine residue of the C-terminal amino acid extension over a cysteine residue outside the C-terminal extension. In certain aspects, the conjugation includes conjugating a linker to a sulfhydryl group of the cysteine residue, e.g., using maleimide reaction chemistry, haloacetyl reaction chemistry, pyridyl disulfide reaction chemistry, or any other suitable reaction chemistry as described elsewhere herein. The methods of making the conjugate may further include reducing the sulfhydryl group of the cysteine residue prior to the conjugating step, e.g., using a suitable reducing agent and reaction conditions as described above. An alternative embodiment of the present disclosure does not require a reduction step as the cysteine within the light chain extension is already in a reduced state as a synthesis product.

In certain aspects, the agent is linked to the cysteine of the C-terminal extension using maleimide reaction chemistry. The maleimide group reacts specifically with sulfhydryl groups when the pH of the reaction mixture is between pH 6.5 and 7.5; the result is formation of a stable thioether linkage. In more alkaline conditions (pH>8.5), primary amines compete with thiols for reaction with maleimides, and also increases the rate of hydrolysis of the maleimide group to a non-reactive maleamic acid. Maleimides do not react with tyrosines, histidines or methionines. Bioconjugation approaches that employ maleimide-based linkers are known and described in detail, e.g., in Hermanson, G. T., Bioconjugate Techniques, 2nd ed. San Diego, Calif. Academic Press 2008; Aslam & Dent, Bioconjugation: Protein Coupling Techniques for the Biomedical Sciences, London Macmillan Reference Ltd 1998; Kalia & Raines, Advances in Bioconjugation, Curr. Org. Chem. 14(2):138-147; and elsewhere.

According to certain embodiments, the agent is linked to the cysteine of the C-terminal extension using haloacetyl reaction chemistry. In certain aspects, a haloacetyl cross-linker that includes an iodoacetyl or a bromoacetyl group is employed. Haloacetyls react with sulfhydryl groups at physiologic pH. The reaction of the iodoacetyl group proceeds by nucleophilic substitution of iodine with a sulfur atom from a sulfhydryl group, resulting in a stable thioether linkage.

In certain aspects, the agent is linked to the cysteine of the C-terminal extension using pyridyl disulfide reaction chemistry. Pyridyl disulfides react with sulfhydryl groups over a broad pH range (with pH 4 to 5 being optimal) to form disulfide bonds. During the reaction, a disulfide exchange occurs between the molecule's —SH group and the reagent's 2-pyridyldithiol group. As a result, pyridine-2-thione is released and can be measured spectrophotometrically (Amax=343 nm) to monitor the progress of the reaction.

To generate a reduced sulfhydryl in the cysteine of the C-terminal amino acid extension to which the agent may be attached (e.g., via a linker), the sulfhydryl group of the cysteine may be contacted with a suitable reducing agent under conditions sufficient to reduce the sulfhydryl group. In certain aspects, the reducing agent is selected from cysteamine hydrochloride, 2-mercaptoethanol, dithiothreitol (DTT), 2-mercaptoethylamine, tris(2-carboxyl)phosphine (TCEP), cysteine HCl, N-ethylmaleimide, Nacystelyn, dornase alfa, thymosin β4, guaifenesin TCEP HCl, and any combination thereof. Reaction conditions for such reducing agents are known in the art and may be optimized, e.g., to promote selectivity or "bias" the reduction of the sulfhydryl group of the cysteine(s) present in the C-terminal extension as opposed to the cysteine residues present in the parental antibody (e.g., the cysteine residues that participate in disulfide bonding between CL and CH1 of the light and heavy chains, and/or between the hinge regions of the heavy chains). An alternative embodiment of the invention does not require a reduction step as the cysteine within the light chain extension is already in a reduced state as a synthesis product.

Preferential reduction of the cysteine(s) of the C-terminal amino acid extension over one or more cysteine residues outside the C-terminal amino acid extension (or exclusive reduction of the cysteine(s) of the C-terminal amino acid extension) may be achieved by selection of suitable reduction conditions. In certain aspects, suitable reduction conditions include suitable selection of one or more of the following: a mild reducing agent and/or a reducing agent having a steric bulk that confers upon the reducing agent a preference for reducing a cysteine of the C-terminal amino acid extension; concentrations of the reducing agent and substrate; the temperature at which the reduction reaction is carried out, the pH of the reduction reaction mixture; the buffer used in the reduction reaction; and/or conditions under which the cells expressing the extended C-terminal light chain polypeptides are cultured (e.g., to obtain free thiol on the C-terminal extension and/or to generate readily reduced intermolecular disulfides). The agent conjugated to the antibody may be any useful agent described elsewhere herein. In certain aspects where the agent is an antibody, the agent may be conjugated to a targeting moiety by antibody conjugation methods described herein.

The ordinarily skilled artisan will appreciate that factors such as pH and steric hindrance (i.e., the accessibility of the amino acid residue to reaction with a reactive partner of interest) are of importance. Modifying reaction conditions to provide for optimal conjugation conditions is well within the skill of the ordinary artisan, and is routine in the art.

In practicing methods according to embodiments of the invention, an effective amount of the active agent is provided in the target cell or cells. In some instances, the effective amount of the modulatory agent is provided in the cell by contacting the cell with the modulatory agent. Contact of the cell with the modulatory agent may occur using any convenient protocol. The protocol may provide for in vitro or in vivo contact of the modulatory agent with the target cell, depending on the location of the target cell. Contact may or may not include entry of the agent into the cell. For example, where the target cell is an isolated cell and the modulatory agent is an agent that modulates expression of target protein, the modulatory agent may be introduced directly into the cell under cell culture conditions permissive of viability of the target cell. Such techniques include, but are not necessarily limited to: viral infection, transfection, conjugation, protoplast fusion, electroporation, particle gun technology, calcium phosphate precipitation, direct microinjection, viral vector delivery, and the like. The choice of method is generally dependent on the type of cell being contacted and the nature of the modulatory agent, and the circumstances under which the transformation is taking place (e.g., in vitro, ex vivo, or in vivo). A general discussion of these methods can be found in Ausubel, et al, Short Protocols in Molecular Biology, 3rd ed., Wiley & Sons, 1995.

Alternatively, where the target cell or cells are part of a multicellular organism, the modulatory agent may be administered to the organism or subject in a manner such that the agent is able to contact the target cell(s), e.g., via an in vivo or ex vivo protocol. By "in vivo," it is meant in the target construct is administered to a living body of an animal. By "ex vivo" it is meant that cells or organs are modified outside of the body. Such cells or organs are typically returned to a living body.

In the subject methods, the active agent(s) may be administered to the targeted cells using any convenient administration protocol capable of resulting in the desired activity. Thus, the agent can be incorporated into a variety of formulations, e.g., pharmaceutically acceptable vehicles, for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments (e.g., skin creams), solutions, suppositories, injections, inhalants and aerosols. As such, administration of the agents can be achieved in various ways, including oral, buccal, rectal, parenteral, intraperitoneal, intradermal, transdermal, intracheal, etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, it may be introduced into tissues or host cells by any number of routes, including viral infection, microinjection, or fusion of vesicles. Jet injection may also be used for intramuscular administration, as described by Furth et al. (1992), *Anal Biochem* 205:365-368. The DNA may be coated onto gold microparticles, and delivered intradermally by a particle bombardment device, or "gene gun" as described in the literature (see, for example, Tang et al. (1992), *Nature* 356:152-154), where gold microprojectiles are coated with the DNA, then bombarded into skin cells. For nucleic acid therapeutic agents, a number of different delivery vehicles find use, including viral and non-viral vector systems, as are known in the art.

Those of skill in the art will readily appreciate that dose levels can vary as a function of the specific compound, the nature of the delivery vehicle, and the like. Preferred dosages for a given compound are readily determinable by those of skill in the art by a variety of means.

In some instances, the methods include employing a paradoxical protocol in order to obtain a desired restoration of neuroendocrine homeostatic function. In certain embodiments, the active agent is administered for a short duration, where by short duration is meant that the administration period lasts for less than about 1 week, e.g., less than about 3 days, e.g., less than about 1 day, e.g., less than about 12 hours, where the duration may be even shorter. The duration refers to the period in which the pharmacological agent from an administered dosage is active. Following administration, as described above, the active agent is removed, e.g., by metabolization of the pharmacological agent, and the subject is permitted to mount a compensatory response. In this following period, no additional stimulus is administered to the subject. The duration of this period between stimulus application, which may be referred to as a "holiday" period, may vary, but in representative embodiments is 1 day or longer, such as 2 days or longer, including 5 days or longer, 10 days or longer, e.g., 15 days or longer. As such, embodiments of the methods include non-chronic (i.e., non-continuous) application of the stimulus, e.g., non-chronic administration of a pharmacologic agent.

In certain embodiments, the methods include close monitoring or supervision of the subject during and/or after application of the stimulus. This monitoring may be completely automated, or at least in part performed manually, e.g., by a health care professional. For example, a health care professional can closely watch the subject following application of the stimulus as well as during the holiday period following stimulus application, and based on this monitoring determine when a next stimulus should be applied. Monitoring also assures that the symptom enhancement is not so severe as to be ultimately damaging to the subject at an unacceptable level. Certain aspects of the monitoring may be automated. For example, following administration, the subject may enter one or more physiological parameters into an automated system, which uses the input parameters to automatically determine whether the subject is staying within a predetermined set of physiological parameters, or whether intervention is necessary. In certain embodiments, the automated monitoring system may also be integrated with a stimulus application device, such that the system, based on monitored parameters, determines when next to administer a stimulus, the duration of the next stimulus, etc. As such, the method may be characterized as applying a first stimulus to the subject and monitoring the subject for a response thereto. Following this first step, the method further includes applying at least a second stimulus to the subject, wherein the second stimulus is determined based on the monitored response to the first stimulus.

In certain embodiments, stimulus to the subject is done in an "irregularly irregular" manner. As such, duration of the stimulus application events, as well as duration of holiday periods between such events, varies randomly over the entire course of a treatment, or at least a portion thereof. In addition, the variation does not follow any pattern, but instead is random.

Subjects

The methods described herein may be employed with a variety of different types of subjects, i.e., animals, where the animals are typically "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In many embodiments, the subjects or patients will be humans.

In some embodiments, the subject has been diagnosed as having a sympathetic or parasympathetic bias mediated condition. In some instances, the methods may include diagnosing the subject as having a sympathetic or parasympathetic bias mediated condition and/or a condition that is modulated by neuroendocrine homeostatic function. Diagnoses of such conditions may be made using any convenient protocol. In some instances, the subject is also one that has been determined to have an autonomic dysfunction. As used herein, the term "autonomic dysfunction" describes any disease or malfunction of the autonomic nervous system. Specific types of autonomic dysfunction of interest include sympathetic and parasympathetic bias. A specific type of parasympathetic bias of interest is vagal bias.

In certain embodiments modulation of at least a portion of a subject's autonomic nervous system is not performed unless one or more aspects of the autonomic nervous system are detected and indicate such modulation is necessary. One aspect that may indicate modulation is necessary is the existence of an autonomic dysfunction, such as parasympathetic bias, e.g., vagal bias.

In certain embodiments the subject has an autonomic dysfunction before diagnosis of an autonomic dysfunction (e.g., sympathetic or parasympathetic bias) occurs. Any suitable physical and/or chemical aspect or indicator of the autonomic nervous system may be employed by one or more of a doctor, nurse, medical professional or individual with appropriate expertise to diagnose an autonomic dysfunction.

An autonomic dysfunction in a subject may be tested for by detecting one or more aspects of the autonomic nervous system as manifested in one or more physiological parameters, e.g., amounts of T helper cells (Th1 and/or Th2), conduction, catecholamine levels, heart rate variability ("HRV"), action potentials, QT interval, particular hormone levels, as well as chronotropic, inotropic, and vasodilator responses. For example, in certain embodiments HRV measures such as low frequency peak ("LF"), high frequency peak ("HF"), and the LF/HF ratio may be used as indicators of different aspects of the autonomic nervous system. In certain embodiments, detection may include detecting the activity or function of a particular organ or system under the control of the autonomic nervous system. Any suitable detection means may be employed to detect relevant information about the autonomic nervous system.

These and other methods and devices for detecting one or more aspects of the autonomic nervous system potentially indicating an autonomic dysfunction that may be employed by embodiments of the subject methods include those described in U.S. Pat. Nos. 7,899,527 and 6,490,480 and U.S. patent Ser. Nos. 10/861,566 and 12/727,560.

In some instances, an aspect of the autonomic nervous system, such as measurable physiological parameters described above (e.g., HRV) may be employed as a measure of homeostatic capacity of the subject. In other words, the autonomic nervous system measurable physiological parameter may be employed as a proxy of or indication of homeostatic capacity of the subject. For example, a given method may include first measuring one or more autonomic nervous system measurable physiological parameters, e.g., HRV, to make an assessment or evaluation of the homeostatic capacity of the subject. If the measured parameter indicates that the homeostatic capacity is not in a desired target range, such as where the subject lacks homeostatic capacity or least adequate or desired homeostatic capacity, e.g., by comparing the measured value to a reference or control, the autonomic nervous system of the subject may then be modulated in a manner effective to restore the homeostatic capacity of the subject, as desired. Following autonomic modulation, an autonomic nervous system measurable physiological parameter, which may be the same or different than the one assessed prior to ANS modulation, may be assessed to determine the effectiveness of the ANS modulation in at least partially restoring homeostatic capacity of the subject.

In some instances, the methods include a step of evaluating homeostatic capacity of the subject. As reviewed above, homeostatic capacity refers to the ability of a subject to maintain relatively constant conditions in the internal environment while continuously interacting with and adjusting to changes originating within or outside the system. By evaluating is meant assessing, analyzing or assaying to provide a form of measurement, e.g., in the form of a determination or proxy thereof, of the homeostatic capacity of the subject. The evaluations that may be made may be quantitative and/or qualitative determinations.

Aspects of the methods of these embodiments include obtaining dynamic biometric data from a subject. The phrase "biometric data" is employed to refer to a measure of a biometric parameter that relates to the physiology of a living organism, e.g., as described below. As such, the biometric parameter which is employed in methods of the invention to obtain the biometric data may be a parameter that provides information about an organism's vital functions, including growth and development, the absorption and processing of nutrients, the synthesis and distribution of proteins and other organic molecules, and the functioning of different tissues, organs, and other anatomic structures. Biometric parameters of interest include, but are not limited to: physical parameters, e.g., blood pressure orthostatic hypotension, pulse pressure, heart rate, heart rate variability (HRV), heart rate recovery, respiration rate, temperature, galvanic skin response, gastrointestinal motility, sleep cycle, VO2 max, bone density, weight, and the like, and combinations thereof; sample analysis obtainable parameters, e.g., pH level, cortisol level, ACTH level, Epinephrine/Norepinephrine level, oxygen saturation, insulin, glucose, inflammatory/immune markers, DNA methylation, DNA double strand breaks, clock genes/factors, oxidative stress, telomere status, gut biome, melatonin level, adenosine level, and the like, and combinations thereof. Dynamic biometric data may be made up of information about a single type of biometric parameter, or two or more different types of biometric parameters. The biometric data employed in methods of the invention may thus be made up of information obtained by measuring or assessing one or more biometric parameters, such as the ones listed above.

As summarized above, the biometric data that is obtained and employed in methods of the invention is dynamic biometric data. By "dynamic biometric data" is meant biometric data that incorporates some type of change component, as opposed to static biometric data. The change component may be temporal and/or in response to an applied stimulus. For example, the dynamic biometric data that is obtained may be biometric data obtained over a given period of time. The given period of time may vary, ranging in some instances from 0.1 seconds to 24 hours, such as 1 second to 12 hours, e.g., 1 second to 1 hour, including 1 second to 1 minute. Where the dynamic biometric data is data obtained over a given period of time, the data may be obtained continuously over that period of time or at one or more distinct points during that period of time. For example, the biometric parameter(s) that is monitored in order to obtain biometric data may be monitored continuously during the given period of time, i.e., it may be obtained in an uninterrupted manner, i.e., without cessation, during the given period of time. Alternatively, the biometric parameter(s) that is monitored in order to obtain biometric data may be monitored intermittently during the given period of time, i.e., it may be obtained at one or more points over the given period of time, with an interval between points at which it is not obtained. In some embodiments, the interval may vary, ranging, for example, from 0.01 sec to 60 minutes or longer, such as 0.1 to 60 s. In some instances, the dynamic biometric data is obtained by evaluating a biometric parameter for a rate of change over a period of time. As such, methods may include obtaining information about the speed at which a biometric parameter of interest changes over a given period of period of time. Obtaining dynamic biometric data as described above provides for numerous benefits, including increases in temporal resolution, as compared to single point in time data. Dynamic biometric data as obtained herein provides a truer and more meaningful measure of the biometric value(s) of interest, as compared to single point in time measurements.

Dynamic biometric data of interest also includes biometric data that is obtained by evaluating a biometric parameter for a change in response to an applied stimulus. Such biometric data may include data that is obtained before and/or after application of the stimulus to the subject. In some instances, the biometric data may be obtained over a given period of time that spans or follows the application of the stimulus to the subject. This type of biometric data may be viewed as biometric data that is obtained over a given period of time in conjunction with application of a stimulus to the subject being evaluated. The applied stimulus may vary, where stimuli of interest include physical stimuli and chemical stimuli. Physical stimuli of interest include, but are not limited to, change in orientation of the subject, exercise, change in temperature experienced by the subject or a portion thereof, and the like. Chemical stimuli of interest include, but are not limited to, administration of various active agents, e.g., orally, topically, by injection or other type of administration route, where active agents of interest include, but are not limited to: sugars, starches, stimulants, and the like.

As reviewed above, a variety of different biometric parameters may be measured to obtain the dynamic biometric data. The method by which the biometric data is obtained may vary depending on the nature of the biometric parameter that is monitored. In some instances, the method employed to obtain the biometric data includes physically monitoring the subject to obtain the dynamic biometric data. For example, physical monitoring of the subject may be employed where the biometric parameter is one or more of blood pressure; orthostatic hypotension; pulse pressure; heart rate; heart rate variability (HRV); heart rate recovery; respiration rate; temperature; VO2 max; bone density; weight; galvanic skin response; sleep cycle; gastrointestinal motility; and combinations thereof. Any convenient protocol for physically monitoring a subject for one or more of the above biometric parameters may be employed, and methods for physically monitoring each are known in the art. For example, where the biometric parameter of interest is HRV, the physical monitoring may include measures such as low frequency peak ("LF"), high frequency peak ("HF"), and the LF/HF ratio to determine HRV and obtain the HRV derived biometric data.

In some embodiments, the dynamic biometric data is obtained by a method that includes analyzing a sample from the subject to obtain the dynamic biometric data. The sample that is analyzed may vary, where samples of interest include, but are not limited to: urine, blood, serum, plasma, saliva, semen, prostatic fluid, nipple aspirate fluid, lachrymal fluid, perspiration, feces, cheek swabs, cerebrospinal fluid, cell lysate samples, amniotic fluid, gastrointestinal fluid, biopsy tissue (e.g., samples obtained from laser capture microdissection (LCM)), and the like. The sample can be a biological sample or can be extracted from a biological sample derived from humans, animals, and the like, and may employ conventional methods for the successful extraction of DNA, RNA, proteins and peptides. In certain embodiments, the sample is a fluid sample, such as a solution of analytes in a fluid. The fluid may be an aqueous fluid, such as, but not limited to water, a buffer, and the like. Biometric parameters that may be monitored by evaluating a sample from the subject include, but are not limited to: pH level; cortisol level; ACTH level; Epinephrine/Norepinephrine level; oxygen saturation; insulin; glucose; inflammatory/immune markers; DNA methylation; DNA double strand breaks; clock genes/factors; oxidative stress; telomere status; gut biome; melatonin level; adenosine level; and combinations thereof. Any convenient protocol for physically monitoring a subject for one or more of the above biometric parameters may be employed, and methods for testing a sample for monitoring each are known in the art.

In some instances, the dynamic biometric data is obtained by both physically monitoring the subject and by assaying a sample from the subject, e.g., as described above.

Aspects of the methods further include evaluating the homoeostatic capacity of the subject from the dynamic biometric data. As such, following obtainment of the dynamic biometric data, the homeostatic capacity of the subject is evaluated based on the obtained dynamic biometric data. Any convenient protocol may be employed to evaluate the homeostatic capacity of the subject based on the obtained dynamic biometric data. For example, the obtained dynamic biometric data may be compared to control or reference sets of dynamic biometric data to obtain the homeostatic capacity evaluation. In some instances, the obtained dynamic biometric data may be compared to a suitable database of control or reference sets to obtain the homeostatic capacity evaluation. The control or references sets of data may be made up of data obtained from multiple different individuals of known homeostatic capacity. The data may be made up from individuals of a variety of different ages and health, including from young and old individuals, as well as healthy and diseased individuals, as desired. Any suitable comparison algorithm may be employed, and the output homeostatic capacity evaluation may be produced in a variety of different formats or configurations. This homeostatic capacity evaluation step may be performed using a suitable functional module of a computing device/system, e.g., as described in greater detail below.

The homeostatic capacity evaluation that is provided by methods of the invention may vary, as desired. For example, the evaluation may be an output in the form of a qualitative assessment, e.g., bad, poor, average, good and exceptional, etc. The output may be in the form of a quantitative assessment, e.g., where the homeostatic capacity evaluation output a number selected from a numerical scale. The homeostatic capacity evaluation output may provide assessment with respect to a number of different homeostatic capacity parameters, such as but not limited to: the robustness, dynamic range, resilience, coping mechanism, anti-fragility, etc., of the homeostatic capacity of the individual. The output showing the homeostatic capacity of the animal/person may be provided as a proxy for the biological age (as opposed to the chronological age) of the subject, e.g., by using statistical correlations relative to the general population. For example, the homeostatic capacity evaluation produced from dynamic biometric data from a 50 year old professional cyclist in great condition could suggest that the "biological age" of that person based on homeostatic capacity measures is actually much younger, e.g., that of a 35 years old from the general population. In some instances, the homeostatic capacity evaluation is one that is prepared by comparing the obtained dynamic biometric data to a database that includes data comprising statistically meaningful values that correlate each biometric value and/or a combination of the biometric values of interest to the values of different ages or age ranges of cohorts for the same biometric value(s). For example, in instances where the obtained biometric data may be from an individual or animal that is 30 years of age, the homeostatic capacity evaluation may be performed by comparing the obtained biometric data to data obtained from healthy individuals from a variety of ages ranging from 20 to 80 years, and show a correlation to a certain age of the individual as a whole or certain systems thereof, e.g., cardiovascular system, neurological system, reproductive system, etc. For example, the output homeostatic capacity evaluating may be an overall composite number, e.g., that the individual has the homeostatic capacity of a 32 year old, or be more granular with respect to particular biological systems of the individual, e.g., where the output is that the system provides a homeostatic capacity evaluation in which the subject has a cardiovascular system of a 25 year old but the nervous system of a 35 year old. In such instances, these sub-categories could be at systems levels of the body and could be more granular, e.g., portions of systems.

Utility

The subject methods find use in the treatment of a variety of different conditions. By treatment is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the condition, or at least symptoms associated therewith, are completely inhibited, e.g. prevented from happening, or stopped, e.g. terminated, such that the subject no longer suffers from the condition, or at least the symptoms that characterize the condition. In certain embodiments, the condition being treated is a disease condition.

In some instances, at least partial restoration of the homoeostatic capacity of a subject results in treatment of a condition caused by sympathetic bias. Conditions that are caused by a sympathetic bias include, but are not limited to aging related diseases, such as but not limited to: cardiovascular disease, cancer, arthritis, cataracts, osteoporosis, type 2 diabetes, hypertension; shy dragers, multi-system atrophy, age related inflammation conditions and diabetes.

In some instances, at least partial restoration of the homoeostatic capacity of a subject results in treatment of a condition caused by parasympathetic bias. Conditions that are caused by a parasympathetic bias include, but are not limited to an allergy, common cold, eczema, asthma, anaphylaxis, attention deficit hyperactive disorder (ADHD), autism, obesity, depression, Tourette's syndrome, hay fever, cough, fatigue, hypothyroidism, chronic fatigue syndrome, environmental sensitivity syndrome, shock, sepsis, food allergy and food allergy syndrome.

Aspects of the invention include treating a food allergy syndrome condition in a subject. As used herein, the term "syndrome" refers to one or more symptoms that are characteristic of a specific disorder or disease. Thus, the phrase "food allergy syndrome" refers to one or more symptoms which are characteristic of or associated with a food allergy.

As such, a food allergy syndrome condition is a condition associated with one or more symptoms characteristic of a food allergy. Accordingly, a food allergy syndrome condition is a condition that is related to reactions caused or exacerbated by a food allergy. Specific food allergy syndrome conditions that may be treated according to embodiments of the invention include, but are not limited to conditions having symptoms associated with the respiratory, digestive, integumentary, cardiovascular, and/or other body systems. In certain embodiments, food allergy syndrome conditions manifest as one or more symptoms, where such symptoms include, but are not limited to: bronchospasm, cough, rhinorrhea, angioedema, gastric hypermotility, urticaria, pruritus, eczema, fatigue, bradycardia, and/or hypotension. As the target condition of the methods described herein is a food allergy syndrome, the subject that is treated by methods of the invention is one that also has one or more food allergies with which the syndrome is associated.

The subject methods find use in a variety of applications in which it is desired to treat a subject for a food allergy syndrome condition, e.g., a food allergy syndrome condition that may be influenced by an abnormality in the subject's autonomic nervous system (e.g., a parasympathetic bias). In such methods, at least a portion of a subject's autonomic nervous system is modulated in a manner suitable to treat the subject for the condition, e.g., in a manner to decrease the parasympathetic activity/sympathetic activity ratio in certain embodiments, e.g., as applied to a portion of the respiratory, digestive, integumentary, cardiovascular, and/or other body systems.

The subject methods find use in the treatment of a variety of different food allergy syndrome conditions in which an abnormality in a subject's homeostatic capacity exists. As reviewed above, by treatment is meant both a prevention and/or at least an amelioration of the symptoms associated with the condition afflicting the subject is achieved, where amelioration is used in a broad sense to refer to at least a reduction in the magnitude of a parameter, e.g., symptom, associated with the food allergy syndrome condition being treated. As such, treatment also includes situations where the condition, or at least symptoms associated therewith, are completely inhibited, e.g. prevented from happening, or stopped, e.g. terminated, such that the subject no longer suffers from the food allergy syndrome condition, or at least the symptoms that characterize the condition.

As noted above, abnormalities in a subject's autonomic nervous system include those characterized by an abnormally high parasympathetic activity or abnormally low parasympathetic activity and/or an abnormally high sympathetic activity or abnormally low sympathetic activity. Certain abnormalities may be characterized by having normal activity in one of the systems of the autonomic nervous system (the parasympathetic system or sympathetic system), but which may have abnormal activity in the other system (the parasympathetic system or sympathetic system).

The subject methods find use in the treatment of a variety of different food allergy syndrome conditions. Such food allergy syndrome conditions include, but are not limited to: conditions associated with the respiratory system including bronchospasm, cough, and rhinorrhea; conditions associated with the digestive system including gastric hypermotility; conditions associated with the integumentary system including angioedema, urticaria, pruritus, atopic dermatitis, and eczema; conditions associated with the circulatory system including fatigue, bradycardia, and hypotension; and combinations thereof.

In some instances, methods of the invention may also result in treatment of symptoms of the food allergy for which the syndrome is associated. Such symptoms may vary, and may include: difficulty swallowing, hives, vomiting, shortness of breath, stomach cramps, runny nose, patches of scaly or itchy skin, nausea, nasal congestion, lightheadedness, rash, diarrhea, fainting, abdominal pain, and swelling of the eyelids, face, lips, tongue or other areas, low blood pressure, blocked airways, and combinations thereof.

In some instances, the method is for the treatment of an aging condition, such as an aging associated condition. In some instances, aging associated conditions are due in part to sympathetic bias. As such, methods provided herein wherein the restoration of a central nervous system endocrine gland modulates sympathetic/parasympathetic bias in the subject is believed to improve such age associated conditions. Aging-associated conditions include, but are not limited to, cardiovascular disease, cancer, arthritis, cataracts, osteoporosis, type 2 diabetes, hypertension; shy dragers, multi-system atrophy, age related inflammation conditions and diabetes. In other instances, aging associated conditions include, but are not limited to: aging-associated disease is selected from the group consisting of cardiovascular disease, cancer, arthritis, cataracts, osteoporosis, type 2 diabetes, hypertension and Alzheimer's disease, hypodynamia, thyroid involution, ectopic calcification, alopecia, skin involution, decrease of growth hormone-producing cells, involution of corpus luteum hormone- and follicle-stimulating hormone-producing cells, degeneration and decrease of Purkinje cells, pulmonary emphysema, osteoporosis, hump back, involution of subcutaneous fat, involution of external genitalia, gonadal involution, abnormality in lipid metabolism, osteoarthritis, lowering of immune function, autoimmune diseases, cataract, hypertension, cerebral apoplexy, myocardial infarction, hyperlipemia, atrophic gastritis, decrease of gastric secretion, disorder of lipid digestion and absorption, dysgeusia, and dysosmia.

In some instances, the condition is a cardiovascular condition. Cardiovascular conditions include, but are not limited to, cardiovascular disease, e.g., atherosclerosis, coronary artery disease, hypertension, hyperlipidemia, eclampsia, pre-eclampsia, cardiomyopathy, volume retention, congestive heart failure, QT interval prolongation, aortic dissection, aortic aneurysm, arterial aneurysm, arterial vasospasm, myocardial infarction, reperfusion syndrome, ischemia, sudden adult death syndrome, arrhythmia, fatal arrhythmias, coronary syndromes, coronary vasospasm, sick sinus syndrome, bradycardia, tachycardia, thromboembolic disease, deep vein thrombosis, coagulopathy, disseminated intravascular coagulation ("DIC"), mesenteric ischemia, syncope, venous thrombosis, arterial thrombosis, malignant hypertension, secondary hypertension, primary pulmonary hypertension, secondary pulmonary hypertension, raynaud's, paroxysmal supraventricular tachycardia, and the like.

In certain embodiments, the subject method is for the treatment of a cancer. Cancers include, but are not limited to, bladder cancer, breast cancer, colon cancer, rectal cancer, endometrial cancer, kidney cancer, leukemia, lung cancer, melanoma, non-Hodgkin lymphoma, pancreatic cancer, prostate cancer and thyroid cancer, and the like.

In some instances, the subject method is for the treatment of arthritis. Arthritic diseases include, but are not limited to, osteoarthritis, rheumatoid arthritis, gout, pseudo-gout, septic arthritis, ankylosing spondylitis, juvenile idiopathic arthritis and Still's disease.

In some instances, the method is for the treatment of an endocrine condition. Endocrine conditions including endocrine diseases, e.g., hypothyroidism, hyperglycemia, diabetes, obesity, syndrome X, insulin resistance, polycystic ovarian syndrome ("PCOS"), and the like.

In other instances, the subject method is for the treatment of a neurodegenerative condition. Neurodegenerative conditions include neurodegenerative diseases, e.g., Alzheimer's Disease, Pick's Disease, Parkinson's Disease, dementia, delirium, amyotrophic lateral sclerosis, and the like.

In yet other instances, the method is for the treatment of a neuroinflammatory condition. Neuroinflammatory conditions include, but are not limited to neuroinflammatory diseases, e.g., viral meningitis, viral encephalitis, fungal meningitis, fungal encephalitis, multiple sclerosis, charcot joint, schizophrenia, myasthenia gravis, and the like.

In some instances, the method is for the treatment of an orthopedic inflammatory condition. Orthopedic inflammatory conditions include orthopedic inflammatory diseases, e.g., osteoarthritis, inflammatory arthritis, regional idiopathic osteoporosis, reflex sympathetic dystrophy, Paget's disease, osteoporosis, antigen-induced arthritis, juvenile chronic arthritis, and the like.

In other instances, the method is for the treatment of a lymphoproliferative condition. Lymphoproliferative conditions include lymphoproliferative diseases, e.g., lymphoma, lymphoproliferative disease, Hodgkin's disease, inflammatory pseudomotor of the liver, and the like.

In yet other instances, the method is for the treatment of an autoimmune condition. Autoimmune conditions include autoimmune diseases, e.g., Graves disease, raynaud's, hashimoto's, takayasu's disease, kawasaki's diseases, arteritis, scleroderma, CREST syndrome, allergies, dermatitis, Henoch-schlonlein purpura, goodpasture syndrome, autoimmune thyroiditis, myasthenia gravis, Reiter's disease, lupus, and the like.

In some embodiments, the method is for the treatment of an inflammatory condition. Inflammatory conditions include, but are not limited to acute respiratory distress syndrome ("ARDS"), multiple sclerosis, rheumatoid arthritis, juvenile rheumatoid arthritis, juvenile chronic arthritis, migraines, chronic headaches, and the like.

In other embodiments, the method is for the treatment of an infection disease. Infectious diseases included, but are not limited to sepsis, viral and fungal infections, diseases of wound healing, wound healing, tuberculosis, infection, AIDS, human immunodeficiency virus, and the like.

In yet other embodiments, the method is for the treatment of a pulmonary condition. Pulmonary conditions include, but are not limited to pulmonary diseases, e.g., tachypnea, fibrotic lung diseases such as cystic fibrosis and the like, interstitial lung disease, desquamative interstitial pneumonitis, non-specific interstitial pneumonitis, intrapulmonary shunts; lymphocytic interstitial pneumonitis, usual interstitial pneumonitis, idiopathic pulmonary fibrosis, pulmonary edema, aspiration, asphyxiation, pneumothorax, right-to-left shunts, left-to-right shunts, respiratory failure, and the like.

In some instances, the method is for the treatment of a transplant-related condition. Transplant-related conditions include transplant related side effects such as transplant rejection, transplant-related tachycardia, transplant related renal failure, transplant related bowel dysmotility, transplant-related hyperreninemia, and the like.

In other instances, the method is for the treatment of a gastrointestinal condition. Gastrointestinal conditions include, but are not limited to, gastrointestinal diseases, e.g., hepatitis, xerostomia, bowel mobility, peptic ulcer disease, constipation, ileus, irritable bowel syndrome, post-operative bowel dysmotility, inflammatory bowel disease, typhlitis, cholelethiasis, cholestasis, fecal incontinence, cyclic vomiting syndrome, and the like.

In yet other instances, the method is for the treatment of a genitourinary condition. Genitourinary conditions including genitourinary diseases, e.g., bladder dysfunction, renal failure, erectile dysfunction, hyperreninemia, hepatorenal syndrome, pulmonary renal syndrome, incontinence, arousal disorder, menopausal mood disorder, premenstrual mood disorder, renal tubular acidosis, pulmonary renal syndrome, and the like.

In other instances, the method is for the treatment of a skin condition, including a skin disease such as wrinkles, cutaneous vasculitis, psoriasis, rash; and the like.

In other embodiments, the method is for the treatment of a neurologic condition, including, but not limited to, a neurologic disease such as epilepsy, depression, schizophrenia, seizures, stroke, insomnia, cerebral vascular accident, transient ischemic attacks, stress, bipolar disorder, concussions, post-concussive syndrome, cerebral vascular vasospasm, central sleep apnea, obstructive sleep apnea, sleep disorders, headaches including chronic headaches, migraines, acute disseminated encephalomyelitis ("ADEM"), and the like.

In yet other embodiments, the method is for the treatment of a pediatric condition, including pediatric diseases such as a respiratory distress syndrome, sudden infant death syndrome, hirschsprung disease, bronchopulmonary dysplasia, congenital megacolon, ananglionosis, juvenile rheumatoid arthritis, juvenile chronic arthritis, and the like.

In some embodiments, the method is for the treatment of a Th-2 dominant condition such as typhlitis, osteoporosis, lymphoma, myasthenia gravis, lupus, and the like.

In some embodiments, the condition is a disease that causes hypoxia, hypercarbia, hypercapnia, acidosis, acidemia, Chronic Obstructive Pulmonary Disease ("COPD"), emphysema, any chronic lung disease that causes acidosis, acute pulmonary embolism, sudden adult death syndrome ("SADS"), chronic pulmonary embolism, pleural effusion, cardiogenic pulmonary edema, non-cardiogenic pulmonary edema, acute respiratory distress syndrome (ARDS), neurogenic edema, hypercapnia, acidemia, asthma, renal tubular, asthma, acidosis, chronic lung diseases that cause hypoxia, hypercarbia or hypercapnia, and the like.

In other embodiments, the condition is an OB-GYN conditions including, but not limited to, an OB-GYN diseases such as amniotic fluid embolism, menopausal mood disorders, premenstrual mood disorders, pregnancy-related arrhythmias, fetal stress syndrome, fetal hypoxia, amniotic fluid embolism, gestational diabetes, pre-term labor, cervical incompetence, fetal distress, peripartum maternal mortality, peripartum cardiomyopathy, labor complications, premenstrual syndrome, dysmenorrheal, endometriosis, and the like.

In yet other embodiments, the subject method is for the treatment of a sudden death syndrome (e.g., sudden adult death syndrome, sudden infant death syndrome, and the like); a menstrual related disorders (e.g., pelvic pain, dysmenorrheal, gastrointestinal disease, nausea, and the like); a peripartum or pregnancy related condition (e.g., peripartum cardiomyopathy, and the like); a fibrosis; a post-operative recovery conditions (e.g., post-operative pain, post operative ileus, post-operative fever, post-operative nausea, and the like); a post-procedural recovery condition (e.g., post-procedural pain, post procedural ileus, post-procedural fever, post-procedural nausea, and the like); a chronic pain; a trauma; hospitalization; glaucoma; male infertility; a disorder of thermoregulation; respiratory sinus arrhythmia; VQ mismatch; or a fibromyalgia; and the like.

In some instances, the subject methods are employed to treat a condition that is caused by an abnormality in the autonomic function of the hypothalamus. In certain instances, the abnormality is a sympathetic bias mediated condition. In other instances, the abnormality is a parasympathetic bias mediated condition. Sympathetic and parasympathetic bias mediated conditions are physiological conditions having one or more undesirable symptoms, where the symptoms arise (at least in part) from sympathetic or parasympathetic bias (at least in a portion of the subject's autonomic nervous system), respectively. Sympathetic and parasympathetic bias mediated conditions include both chronic and acute conditions. In some instances, the conditions of interest are disease conditions. In some instances, the conditions of interest are conditions arising in response to one or more stimuli, e.g., ingestion of nutritional or therapeutic compositions, exposure to certain environmental conditions, infection with a pathogenic agent, induction of stress, e.g., from exercise, etc. Conditions that are caused by a sympathetic bias include, but are not limited to aging related diseases (e.g., cardiovascular disease, cancer, arthritis, cataracts, osteoporosis, type 2 diabetes, hypertension; shy dragers, multi-system atrophy, age related inflammation conditions and diabetes). Conditions that are caused by a parasympathetic bias include, but are not limited to an allergy, common cold eczema, asthma, anaphylaxis, attention deficit hyperactive disorder (ADHD), autism, obesity, depression, and food allergy.

Other conditions may also be treated in accordance with the subject invention. Embodiments of the subject invention include treating one or more conditions, sequentially or at the same time, in accordance with the subject invention.

With respect to evaluation of homeostatic capacity methods of the invention, such methods find use in a variety of different applications. Applications of interest include, but are not limited to: health and wellness monitoring applications; diagnostic applications; treatment applications, e.g., as described above; etc. For example, the methods described herein may be employed in various health and wellness monitoring applications, e.g., by individuals monitoring themselves or interested stakeholders, e.g., health care professionals, physical trainers, family or friends, etc., monitoring the individuals. For example, the methods may be employed by individuals to monitor their homeostatic capacity on an ongoing basis, e.g., so that they can monitor their health and well-being over time. The individuals may use the homeostatic capacity evaluation to make lifestyle changes, e.g., changes in diet and/or exercise. Alternatively or in addition, the methods may be employed by a stakeholder having an interest in the health of an individual, such as the stakeholders listed above.

In yet other instances, the methods may be employed in at least the prediction of the presence of, if not diagnosis of, a homeostatic capacity disease condition in a subject. For example, in some embodiments the homeostatic capacity evaluation may be employed to predict, if not diagnose, the presence of a sympathetic or parasympathetic bias mediated condition in the subject. In some instances, the prediction, if not diagnosis, may be of an autonomic dysfunction condition in the subject. As used herein, the term "autonomic dysfunction" describes any disease or malfunction of the autonomic nervous system. Specific types of autonomic dysfunction of interest include sympathetic and parasympathetic bias. A specific type of parasympathetic bias of interest is vagal bias.

In some instances, the methods find use as a component of the treatment of a variety of different conditions, e.g., as described above. By treatment is meant that at least an amelioration of the symptoms associated with the condition afflicting the subject is achieved, where amelioration is used in a broad sense to refer to at least a reduction in the magnitude of a parameter, e.g. symptom, associated with the condition being treated. As such, treatment also includes situations where the condition, or at least symptoms associated therewith, are completely inhibited, e.g. prevented from happening, or stopped, e.g. terminated, such that the subject no longer suffers from the condition, or at least the symptoms that characterize the condition. In certain embodiments, the condition being treated is a disease condition.

In some instances, at least partial restoration of the homoeostatic capacity of a subject results in treatment of a condition caused by sympathetic bias. Conditions that are caused by a sympathetic bias include, but are not limited to aging related diseases, such as but not limited to: cardiovascular disease, cancer, arthritis, cataracts, osteoporosis, type 2 diabetes, hypertension; shy dragers, multi-system atrophy, age related inflammation conditions and diabetes.

In some instances, at least partial restoration of the homoeostatic capacity of a subject results in treatment of a condition caused by parasympathetic bias. Conditions that are caused by a parasympathetic bias include, but are not limited to an allergy, common cold, eczema, asthma, anaphylaxis, attention deficit hyperactive disorder (ADHD), autism, obesity, depression, Tourette's syndrome, hay fever, cough, fatigue, hypothyroidism, chronic fatigue syndrome, environmental sensitivity syndrome, shock, sepsis, food allergy and food allergy syndrome.

Devices

A number of different devices and systems may be employed in accordance with the subject invention. Devices and systems which may be adapted for use in the subject invention include devices and systems for applying at least one pharmacological agent to a subject and devices and systems for applying electrical energy to a subject.

Devices and Systems for Applying Pharmacological Agent(s)

Different devices and systems for applying one or more pharmacological agents to a subject which may be adapted for use in the subject invention include embodiments configured to deliver pharmacological agent(s) using any of the methods described above. A device for applying one or more pharmacological agents to modulate autonomic function is a "pharmacological modulator".

Embodiments may include an implantable or external pharmacological delivery device such as, but not limited to, pumps, epidural injectors, syringes or other injection apparatus, catheter and/or reservoir operatively associated with a catheter, etc. For example, in certain embodiments a delivery device employed to deliver at least one pharmacological agent to a subject may be a pump, syringe, catheter or reservoir operably associated with a connecting device such as a catheter, tubing, or the like. Containers suitable for delivery of at least one pharmacological agent to a pharmacological agent administration device include instruments of containment that may be used to deliver, place, attach, and/or insert the at least one pharmacological agent into the delivery device for administration of the pharmacological agent to a subject and include, but are not limited to, vials, ampules, tubes, capsules, bottles, syringes and bags.

In some embodiments, the device for applying one or more pharmacological agents includes a sensor for detecting a food allergy syndrome, condition, symptom and/or instigator. As used herein, an "instigator" is an aspect that causes or aggravates a food allergy syndrome condition and/or symptom. A sensor may take the form of an electrode or the like and may be configured specifically to detect one or more symptoms of a food allergy condition. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. More detailed descriptions of sensors that may be employed in the practice of the subject invention, and other examples of sensors that may be employed are disclosed in U.S. Pat. No. 5,716,377, which is incorporated herein by reference. Systems for applying at least one pharmacological agent according to the methods described above are made up of one or more of the devices or components listed or incorporated by reference herein.

Devices and systems for applying at least one pharmacological agent to a subject and which may be adapted for use in the subject invention are described, e.g., in U.S. Pat. Nos. 7,363,076; 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; 4,585,452; U.S. patent application Ser. Nos. 10/748,897; 10/748,976; 10/871,366; 10/846,486 10/917,270; 10/962,190; 11/060,643 11/251,629; 11/238,108; 11/592,027; 60/654,139; 60/702,776; and elsewhere, the disclosures of which are herein incorporated by reference.

Devices and Systems for Applying Electrical Energy

Devices and systems for applying electrical energy to a subject which may be adapted for use in the subject invention include embodiments configured to deliver electrical energy using any of the methods described above. In accordance with the subject methods to apply electrical energy to a subject, once operatively positioned, the electric energy applying device is activated to provide an electrical signal to the targeted area in a manner effective to practice the subject methods.

A device for applying electrical energy to modulate autonomic function is an "electrical modulator". Electrical modulators may be positioned directly on a targeted area and may be implantable within the body of the subject or be wholly or partially external to the subject's body. An electrical energy applying device or system typically includes a stimulator such as one or more electrodes, a controller or programmer and one or more connectors for connecting the stimulating device to the controller.

The one or more electrodes employed in the subject invention are controllable to provide output signals that may be varied in voltage, frequency, pulse width, current and intensity. The energy source for the electrical output may be provided by a battery or generator that is operatively connected to the electrode(s). The energy source may be positioned in any suitable location such as adjacent to the electrode(s), or a remote site in or on the subject's body or away from the subject's body in a remote location and the electrode may then be connected to the remotely positioned energy source using wires. A controller or programmer may also be coupled with an electric energy applying device. The programmer is typically one or more microprocessors under the control of a suitable software program.

In some embodiments, the device for applying electrical energy includes a sensor for detecting a food allergy syndrome condition symptom and/or instigator. As used herein, an "instigator" is an aspect that causes or aggravates a food allergy syndrome condition and/or symptom. A sensor may take the form of an electrode or the like and may be configured specifically to detect one or more symptoms of a food allergy condition. Signals received by such a sensor may be amplified before further processing. A sensor may also take the form of a device capable of detecting nerve compound action potentials or may take the form of a transducer that includes an electrode with an ion selective coating applied which is capable of directly transducing the amount of a particular transmitter substance or its breakdown by-products. More detailed descriptions of sensors that may be employed in the practice of the subject invention, and other examples of sensors that may be employed are disclosed in U.S. Pat. No. 5,716,377, which is incorporated herein by reference. Systems for applying electrical energy according to the methods described above are made up of one or more of the devices or components listed or incorporated by reference herein.

In embodiments in which electrical energy is used, any suitable protocol may be used, where certain protocols include using an electric energy applying device to deliver a suitable amount of electrical energy to a subject. Once an electric energy applying device is positioned in a suitable position on or about one or more targeted areas electrical energy is applied thereto for a period of time sufficient to provide the desired effect.

A number of different devices and systems for applying electrical energy to a subject and which may be adapted for use in the subject invention are described, e.g., in U.S. Pat. No. 7,149,574; U.S. Pat. No. 7,711,430; U.S. Pat. No. 7,363,076; U.S. patent application Ser. Nos. 10/661,368; 10/748,976; 10/871,366; 10/846,486 10/917,270; 10/962,190; 11/060,643 11/251,629; 11/238,108; 11/592,027; 60/654,139; and 60/702,776; and elsewhere, the disclosures of which are herein incorporated by reference.

Devices for Evaluating Homeostatic Capacity

A number of different devices and systems may be employed to evaluate homeostatic capacity in accordance with embodiment of the invention. Devices and systems that may be adapted or configured for use in the subject invention include devices and systems for obtaining dynamic biometric data from a subject and making a homeostatic capacity evaluation of the subject based on the obtained dynamic biometric data. Devices of interest may include one or more functional modules, which may be distributed among two or more distinct hardware units or integrated into a single hardware unit. In some instances, the devices include a dynamic biometric data obtainment module, a processor unit module; and a homeostatic capacity evaluation output module. The dynamic biometric obtainment module is adapted to obtain dynamic biometric data, e.g., by being in operational communication with one or more biometric parameter sensors and or an input configured to receive dynamic biometric data from a source of such data, and transmit the obtained biometric data to the process unit module. The processor unit module is adapted to retrieve the dynamic biometric data from the dynamic biometric data obtainment module and make a homeostatic capacity evaluation therefrom. As such, the processor module is configured to produce a homeostatic capacity evaluation from the received or input dynamic biometric data. Accordingly, the processor module may also be identified as the homeostatic capacity evaluation module. The output module is adapted to provide the homeostatic capacity evaluation to a user, e.g., the subject or interested stakeholder. In some instances, the output module is configured to display the homeostatic capacity evaluation to a user, e.g., via graphical user interface (GUI). In one embodiment, a visual display can be used for displaying the homeostatic capacity evaluation. Other outputs may also be employed, e.g., printouts, messages (e.g., text messages or emails) sent to another display device, to a storage location for later viewing (e.g., the cloud), etc.

As would be recognized by one of skilled in the art, many different software, firmware, hardware options and data structures can be employed in devices of the invention, e.g., as described above. In some instances, a general-purpose computer can be configured to a functional arrangement for the methods and programs disclosed herein. The hardware architecture of such a computer is well known by a person skilled in the art, and can comprise hardware components including one or more processors (CPU), a random-access memory (RAM), a read-only memory (ROM), an internal or external data storage medium (e.g., hard disk drive). A computer system can also comprise one or more graphic boards for processing and outputting graphical information to display means. The above components can be suitably interconnected via a bus inside the computer. The computer can further comprise suitable interfaces for communicating with general-purpose external components such as a monitor, keyboard, mouse, network, etc. In some embodiments, the computer can be capable of parallel processing or can be part of a network configured for parallel or distributive computing to increase the processing power for the present methods and programs. In some embodiments, the program code read out from the storage medium can be written into a memory provided in an expanded board inserted in the computer, or an expanded unit connected to the computer, and a CPU or the like provided in the expanded board or expanded unit can actually perform a part or all of the operations according to the instructions of the program code, so as to accomplish the functions described below. In other embodiments, the method can be performed using a cloud computing system. In these embodiments, the data files and the programming can be exported to a cloud computer, which runs the program, and returns an output to the user.

The memory of a computer system can be any device that can store information for retrieval by a processor, and can include magnetic or optical devices, or solid-state memory devices (such as volatile or non-volatile RAM). A memory or memory unit can have more than one physical memory device of the same or different types (for example, a memory can have multiple memory devices such as multiple drives, cards, or multiple solid state memory devices or some combination of the same). With respect to computer readable media, "permanent memory" refers to memory that is permanent. Permanent memory is not erased by termination of the electrical supply to a computer or processor. Computer hard-drive ROM (i.e., ROM not used as virtual memory), CD-ROM, floppy disk and DVD are all examples of permanent memory. Random Access Memory (RAM) is an example of non-permanent (i.e., volatile) memory. A file in permanent memory can be editable and re-writable. Operation of the computer is controlled primarily by operating system, which is executed by a central processing unit. The operating system can be stored in a system memory. In some embodiments, the operating system includes a file system. In addition to the operating system, one possible implementation of the system memory includes a variety programming files and data files for implementing the method described above.

In use, dynamic biometric data information is input into the system, and a user receives a homeostatic capacity evaluation from the system, e.g., as described above. In certain embodiments, instructions in accordance with the method (e.g., in the form of a mobile app or other type of structure) described herein can be coded onto a computer-readable medium in the form of "programming", where the term "computer readable medium" as used herein refers to any storage or transmission medium (including non-transitory version so such) that participates in providing instructions and/or data to a computer for execution and/or processing. Examples of storage media include a floppy disk, hard disk, optical disk, magneto-optical disk, CD-ROM, CD-R, magnetic tape, non-volatile memory card, ROM, DVD-ROM, Blue-ray disk, solid state disk, and network attached storage (NAS), whether or not such devices are internal or external to the computer. A file containing information can be "stored" on computer readable medium, where "storing" means recording information such that it is accessible and retrievable at a later date by a computer. The computer-implemented method described herein can be executed using programming that can be written in one or more of any number of computer programming languages. Such languages include, for example, Java (Sun Microsystems, Inc., Santa Clara, Calif.), Visual Basic (Microsoft Corp., Redmond, Wash.), and C++ (AT&T Corp., Bedminster, N.J.), as well as any many others.

As mentioned above, the functional modules may be performed by a variety of different hardware, firmware and software configurations. In some instances, the functional modules will be distributed among a system of two or more distinct devices, which may be in communication with each other, e.g., via wired or wireless communication. In other instances, the distinct functional modules will be integrated into a single device. Where the distinct functional modules are integrated into a single device, the device may have a variety of configurations. For example, the device may be a laboratory device, which may or may not be configured to a bench top device. In yet other instances, the device may be a handheld device, e.g., a smartphone or tablet type device. In yet other instances, the device may be a wearable device, such as a watch type device, a wearable patch type device, etc.

Notwithstanding the appended clauses, the disclosure set forth herein is also defined by the following clauses:

1. A method of at least partially restoring homeostatic capacity of a subject, the method comprising:
modulating at least a portion of subject's autonomic nervous system in a manner sufficient to at least partially restore homeostatic capacity of the subject.
2. The method according to Clause1, wherein homeostatic capacity is restored in the subject in 48 hours or less following onset of the modulating.
3. The method according to Clause2, wherein homeostatic capacity is restored in the subject in 24 hours or less following onset of the modulating.
4. The method according to any of Clauses 1 to 3, wherein the method comprises increasing the sympathetic/parasympathetic activity ratio of the subject.
5. The method according to any of Clauses 1 to 3, wherein the method comprises increasing the parasympathetic/sympathetic activity ratio of the subject.
6. The method according to any of Clauses 1 to 5, wherein the subject's autonomic nervous system is modulated via an electrical protocol.
7. The method according to any of the preceding clauses, wherein the subject's autonomic nervous system is modulated via a pharmacological protocol.
8. The method according to any of the preceding clauses, wherein the method comprises determining that the subject lacks autonomic homeostasis prior to modulating the subject's autonomic nervous system.
9. The method according to Clause8, wherein determining that the subject lacks homeostasis comprises assaying a physiological parameter of the subject and employing the parameter to determine that the subject lacks autonomic homeostasis.
10. The method according to Clause9, wherein the physiological parameter is heart rate variability.
11. The method according to any of the preceding clauses, wherein the method further comprises determining whether autonomic homeostasis has been at least partially restored.
12. The method according to Clause11, wherein the determining whether autonomic homeostasis has been restored comprises assaying a physiological parameter of the subject and employing the parameter to determine whether autonomic homeostasis has been restored.
13. The method according to Clause12, wherein the parameter is heart rate variability.
14. The method according to any of the preceding clauses, wherein the method is a method of treating a subject for a condition.
15. The method according to Clause14, wherein the condition is a disease condition.
16. The method according to Clause15, wherein the disease condition is selected from the group consisting of allergy, common cold, eczema, asthma, anaphylaxis, attention deficit hyperactive disorder (ADHD), autism, obesity, depression, Tourette's syndrome, hay fever, cough, fatigue, hypothyroidism, chronic fatigue syndrome, environmental sensitivity syndrome, shock, sepsis, food allergy and food allergy syndrome.
17. The method according to any of the preceding clauses wherein the subject is a mammal.
18. The method according to Clause17, wherein the subject is a human.

Notwithstanding the appended clauses, the disclosure set forth herein is also defined by the following clauses:

1. A method of treating a living subject for a condition, the method comprising:
administering to the subject an amount of an apoptosis modulator effective to at least partially restore homeostatic function of the neuroendocrine system to treat the subject for the condition.
2. The method according to Clause 1, wherein the apoptosis modulator is an apoptosis inhibitor.
3. The method according to Clause 2, wherein the apoptosis inhibitor exhibits inhibitory activity on an extrinsic apoptotic pathway.
4. The method according to Clause 2, wherein the apoptosis inhibitor exhibits inhibitory activity on an intrinsic apoptotic pathway.
5. The method according to Clause 2, wherein the apoptosis inhibitor is not a caspase inhibitor.
6. The method according to any of Clauses 1 to 5, wherein the condition is an aging condition.
7. The method according to Clause 6, wherein the aging condition is an aging-associated disease.

8. The method according to Clause 7, wherein the aging-associated disease is selected from the group consisting of cardiovascular disease, cancer, arthritis, cataracts, osteoporosis, type 2 diabetes, hypertension and Alzheimer's disease, hypodynamia, thyroid involution, ectopic calcification, alopecia, skin involution, decrease of growth hormone-producing cells, involution of corpus luteum hormone- and follicle-stimulating hormone-producing cells, degeneration and decrease of Purkinje cells, pulmonary emphysema, osteoporosis, hump back, involution of subcutaneous fat, involution of external genitalia, gonadal involution, abnormality in lipid metabolism, osteoarthritis, lowering of immune function, autoimmune diseases, cataract, hypertension, cerebral apoplexy, myocardial infarction, hyperlipemia, atrophic gastritis, decrease of gastric secretion, disorder of lipid digestion and absorption, dysgeusia, and dysosmia.

9. The method according to any of Clauses 1 to 8, wherein the subject is a mammal.

10. The method according to Clause 9, wherein the mammal is a human.

11. The method according to Clause 9, wherein the apoptosis modulator is chronically administered to the subject.

12. The method according to any of Clauses 1 to 10, wherein the method results in a restoration of neuroendocrine homeostatic function that is closer to that of a healthy human 25 year old.

13. The method according to any of Clauses 1 to 12, wherein the method results in a modulation of autonomic function of the subject.

14. The method according to Clause 13, wherein the autonomic function is modulated so that the sympathetic/parasympathetic bias of the subject is closer to the sympathetic/parasympathetic bias of a healthy human 25 year old.

15. The method according to any of Clauses 1 to 14, wherein the method results in a restoration of pituitary function so that the pituitary function is closer to that of a healthy human 25 year old.

16. The method according to any of the previous clauses, wherein the method comprises inhibiting apoptosis of cells of the endocrine gland.

17. The method according to Clause 16, wherein the method further comprises inhibiting apoptosis of non-endocrine gland cells.

Notwithstanding the appended clauses, the disclosure set forth herein is also defined by the following clauses:

1. A method of evaluating homoeostatic capacity of a subject, the method comprising:
    obtaining dynamic biometric data from the subject; and
    evaluating the homoeostatic capacity of the subject from the dynamic biometric data.

2. The method according to Clause 1, wherein the dynamic biometric data comprises biometric data obtained over a period of time.

3. The method according to Clause 2, wherein the biometric data is continuously obtained over the period of time.

4. The method according to Claus 1, wherein the dynamic biometric data is obtained by evaluating a biometric parameter for a change in response to an applied stimulus.

5. The method according to Clause 4, wherein the applied stimulus comprises a physical stimulus.

6. The method according to Clause 4, wherein the applied stimulus comprises a chemical stimulus.

7. The method according to Clause 1, wherein the dynamic biometric data is obtained by evaluating a biometric parameter for a rate of change over a period of time.

8. The method according to any of the preceding clauses, wherein the method comprises physically monitoring the subject to obtain the dynamic biometric data.

9. The method according to any of the preceding clauses, wherein the method comprises analyzing a sample from the subject to obtain the dynamic biometric data.

10. The method according to any of the preceding clauses, wherein the biometric data is obtained for a biometric parameter selected from the group consisting of blood pressure; orthostatic hypotension; pulse pressure; heart rate; heart rate variability; heart rate recovery; respiration rate; temperature; pH level; cortisol level; ACTH level; Epinephrine/Norepinephrine level; galvanic skin response; oxygen saturation; insulin; glucose; inflammatory/immune markers; DNA methylation; DNA double strand breaks; clock genes/factors; oxidative stress; telomere status; gastrointestinal motility; gut biome; melatonin level; adenosine level; sleep cycle; VO2 max; bone density; weight; and combinations thereof.

11. The method according to any of the preceding clauses, wherein the subject is a mammal.

12. The method according to Clause 11, wherein the subject is a primate.

13. The method according to Clause 12, wherein the subject is a human.

14. The method according to Clause 11, wherein the subject is a laboratory research animal.

15. The method according to any of the preceding clauses, wherein the method further comprises modulating the homoeostatic capacity of the subject.

16. The method according to Clause 15, wherein the homeostatic capacity of the subject is modulated to approximate that of a young adult.

17. The method according to any of Clauses 15 and 16, wherein the homoeostatic capacity of the subject is pharmacologically modulated.

18. The method according to any of Clauses 15 and 16, wherein the homoeostatic capacity of the subject is electrically modulated.

19. A device configured to evaluate a subject's homoeostatic capacity, the device comprising:
    an input for receiving dynamic biometric data from a subject;
    a homeostatic capacity evaluation module configured to evaluate the homoeostatic capacity of the subject from input dynamic biometric data; and
    an output configured to provide a homoeostatic capacity evaluation of a subject.

20. The device according to Clause 19, wherein the dynamic biometric data comprises biometric data as described in any of Clauses 1 to 10.

All publications and patent applications mentioned in this specification are herein incorporated by reference to the same extent as if each individual publication or patent application was specifically and individually indicated to be incorporated by reference.

The invention now being fully described, it will be apparent to one of skill in the art that many changes and modifications can be made thereto without departing from the spirit and scope of the appended claims.

What is claimed is:

1. A method of at least partially restoring homeostatic capacity of the neuroendocrine system of a subject, the method comprising:
    modulating at least a portion of a central nervous system endocrine gland of the subject by administering a pharmacological stimulus comprising an apoptosis modulator that selectively targets neuroendocrine cells in a manner sufficient to modulate the sympathetic activity/parasympathetic activity ratio of the subject and thereby at least partially restore homeostatic capacity of the neuroendocrine system of the subject.

2. The method according to claim 1, wherein homeostatic capacity is restored in the subject in 48 hours or less following onset of the modulating.

3. The method according to claim 1, wherein the apoptosis modulator is an apoptosis inhibitor.

4. The method according to claim 3, wherein the apoptosis inhibitor is a general apoptotic pathway inhibitor.

5. The method according to claim 3, wherein the apoptosis inhibitor is an extrinsic apoptotic pathway inhibitor.

6. The method according to claim 3, wherein the apoptosis inhibitor is an intrinsic apoptotic pathway inhibitor.

7. The method according to claim 1, wherein the method comprises determining that the subject lacks autonomic homeostasis prior to modulating the subject's autonomic nervous system.

8. The method according to claim 7, wherein determining that the subject lacks homeostasis comprises assaying a physiological parameter of the subject and employing the parameter to determine that the subject lacks autonomic homeostasis.

9. The method according to claim 8, wherein the physiological parameter is heart rate variability.

10. The method according to claim 1, wherein the method comprises evaluating homeostatic capacity of the subject by:
obtaining dynamic biometric data from the subject; and
evaluating the homeostatic capacity of the subject from the dynamic biometric data.

11. The method according to claim 10, wherein the dynamic biometric data comprises biometric data obtained over a period of time.

12. The method according to claim 11, wherein the biometric data is continuously obtained over the period of time.

13. The method according to claim 10, wherein the dynamic biometric data is obtained by evaluating a biometric parameter for a change in response to an applied stimulus.

14. The method according to claim 10, wherein the dynamic biometric data is obtained by evaluating a biometric parameter for a rate of change over a period of time.

15. The method according to claim 10, wherein the method comprises physically monitoring the subject to obtain the dynamic biometric data.

16. The method according to claim 10, wherein the method comprises analyzing a sample from the subject to obtain the dynamic biometric data.

17. The method according to claim 1, wherein the method is a method of treating the subject for a condition.

18. The method according to claim 17, wherein the condition is a disease condition.

19. The method according to claim 17, wherein the condition is an aging condition.

20. The method according to claim 19, wherein the aging condition is an aging-associated disease.

* * * * *

UNITED STATES PATENT AND TRADEMARK OFFICE
CERTIFICATE OF CORRECTION

PATENT NO.  : 10,835,134 B2
APPLICATION NO. : 14/737248
DATED : November 17, 2020
INVENTOR(S) : Yun et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 626 days.

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*